US011536255B1

(12) United States Patent
Rowe

(10) Patent No.: US 11,536,255 B1
(45) Date of Patent: Dec. 27, 2022

(54) HYBRID ACTUATION DEVICE INCLUDING FLUIDLY COOLED SMA WIRES

(71) Applicant: Toyota Motor Engineering & Manufacturing North America, Inc., Plano, TX (US)

(72) Inventor: Michael P. Rowe, Pinckney, MI (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 0 days.

(21) Appl. No.: 17/691,794

(22) Filed: Mar. 10, 2022

(51) Int. Cl.
| | |
|---|---|
| *F03G 7/06* | (2006.01) |
| *A61F 2/08* | (2006.01) |
| *B25J 9/10* | (2006.01) |
| *A61F 2/50* | (2006.01) |

(52) U.S. Cl.
CPC ............ *F03G 7/06143* (2021.08); *A61F 2/08* (2013.01); *B25J 9/1085* (2013.01); *F03G 7/062* (2021.08); *F03G 7/06112* (2021.08); *A61F 2002/0894* (2013.01); *A61F 2002/5066* (2013.01)

(58) Field of Classification Search
CPC .. F03G 7/06143; F03G 7/06112; F03G 7/062; A61F 2/08; A61F 2002/0894; A61F 2002/5066; B25J 9/1085
USPC .............. 60/527–529; 310/305–309; 623/26, 623/14.13
See application file for complete search history.

(56) References Cited

U.S. PATENT DOCUMENTS

| | | | |
|---|---|---|---|
| 6,530,217 B1 | 3/2003 | Yokota et al. | |
| 7,446,450 B2 * | 11/2008 | Boland | H02N 1/08 310/11 |
| 8,362,882 B2 | 1/2013 | Heubel et al. | |
| 8,695,334 B2 | 4/2014 | Lewis et al. | |
| 9,662,197 B2 * | 5/2017 | Yun | B25J 9/1075 |
| 10,302,586 B2 * | 5/2019 | Sun | G01N 27/305 |
| 10,995,779 B2 * | 5/2021 | Keplinger | H02N 1/006 |
| 11,353,009 B1 * | 6/2022 | Rowe | F03G 7/06 |
| 2021/0237809 A1 * | 8/2021 | Rowe | B62D 25/18 |

FOREIGN PATENT DOCUMENTS

| | | |
|---|---|---|
| KR | 20210086518 A | 7/2021 |
| WO | 2021118185 A2 | 6/2021 |

* cited by examiner

*Primary Examiner* — Hoang M Nguyen
(74) *Attorney, Agent, or Firm* — Dinsmore & Shohl LLP

(57) ABSTRACT

A hybrid actuation device includes an artificial muscle, a first plate coupled to a second plate, and a shape memory alloy wire. The artificial muscle includes a housing, a first electrode and a second electrode, and a dielectric fluid. The housing includes a first film layer, a second film layer, an electrode region, and an expandable fluid region. The first electrode and the second electrode are each disposed in the electrode region of the housing. The dielectric fluid is disposed within the housing. The first plate and the second plate are positioned within the housing, the first plate positioned between the first film layer and the first electrode, and the second plate positioned between the second film layer and the second electrode. The shape memory alloy wire extends from the first plate to the second plate and through the dielectric fluid.

20 Claims, 10 Drawing Sheets

HYBRID ACTUATION DEVICE INCLUDING FLUIDLY COOLED SMA WIRES

TECHNICAL FIELD

The present specification generally relates to hybrid actuation devices that include shape memory alloy materials and artificial muscles.

BACKGROUND

Current robotic technologies rely on rigid components, such as servomotors to perform tasks, often in a structured environment. This rigidity presents limitations in many robotic applications, caused, at least in part, by the weight-to-power ratio of servomotors and other rigid robotics devices. The field of soft robotics improves on these limitations by using artificial muscles and other soft actuators. Artificial muscles attempt to mimic the versatility, performance, and reliability of a biological muscle. Some artificial muscles rely on fluid-based actuators. For example, certain artificial muscles may introduce fluid into and out of a volume to expand or contract the artificial muscles to perform mechanical work on a load. However, these amount of force that current artificial muscles can exert is limited. Additionally, these artificial muscles may require time to recover between actuation.

Accordingly, a need exists for improved actuation devices that include artificial muscles and reduce recovery time, thereby improving the life of the actuation devices.

SUMMARY

In one embodiment, a hybrid actuation device includes an artificial muscle, a first plate coupled to a second plate, and a shape memory alloy wire. The artificial muscle includes a housing, a first electrode and a second electrode, and a dielectric fluid. The housing includes a first film layer, a second film layer, an electrode region, and an expandable fluid region. The first electrode and the second electrode are each disposed in the electrode region of the housing. The dielectric fluid is disposed within the housing. The first plate and the second plate are positioned within the housing, the first plate positioned between the first film layer and the first electrode, and the second plate positioned between the second film layer and the second electrode. The shape memory alloy wire extends from the first plate to the second plate and through the dielectric fluid.

In another embodiment, a hybrid actuation device includes an artificial muscle, a plate system, and a shape memory alloy wire. The artificial muscle includes a housing, a first electrode and a second electrode, and a dielectric fluid. The housing has an electrode region and an expandable fluid region. The first electrode and the second electrode are each disposed in the electrode region of the housing. A central opening is formed in each of the first electrode and the second electrode and encircles the expandable fluid region. The dielectric fluid is disposed within the housing. The plate system includes a plurality of plate pairs, each of the plurality of plate pairs comprising a first plate coupled to a second plate, the first plate and the second plate positioned within the housing. The shape memory alloy wire is coupled to at least one first plate of the plurality of plate pairs, and positioned within the central opening of the first electrode and the second electrode.

In yet another embodiment, a method of actuating a hybrid actuation device includes actuating a shape memory alloy wire that is coupled to a first plate and a second plate, thereby drawing the first plate and the second plate together and placing the hybrid actuation device in an actuated state, and applying a voltage to a first electrode and a second electrode, thereby electrostatically attracting the first electrode and the second electrode together to hold the hybrid actuation device in the actuated state. An artificial muscle is at least partially positioned between the first plate and the second plate, the artificial muscle including a housing, the first electrode and the second electrode, and a dielectric fluid. The housing includes a first film layer, a second film layer, an electrode region, and an expandable fluid region. The first electrode and the second electrode are each disposed in the electrode region of the housing. The dielectric fluid is disposed within the housing. The shape memory alloy wire extends from the first plate to the second plate and extends through the dielectric fluid. The first plate is positioned within the housing between the first film layer and the first electrode, and the second plate is positioned within the housing between the second film layer and the second electrode.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1A:
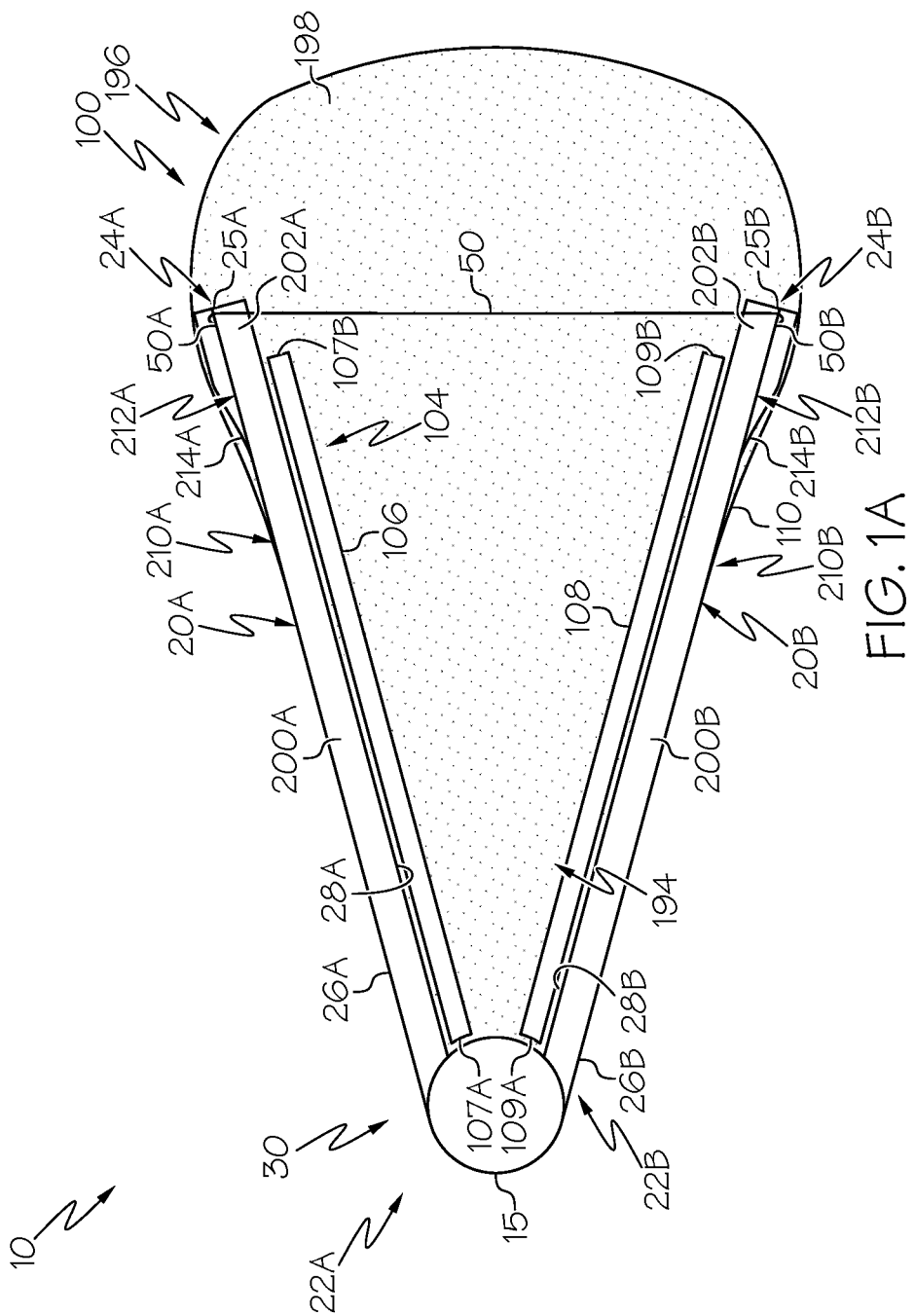
FIG. 1A schematically depicts a side view of a hybrid actuation device in a non-actuated state, according to one or more embodiments shown and described herein.

Embodiments described herein are directed to hybrid actuation devices that include a shape memory alloy (SMA) wire and an artificial muscle. The artificial muscle is positioned between and coupled to a plate pair comprising a first plate and a second plate that are hinged or otherwise coupled together along an end of the plate pair. The artificial muscle may be a self-contained, fluidic artificial muscle. For example, the artificial muscle includes a housing having an electrode region and an expandable fluid region, a first electrode and a second electrode each disposed in the electrode region of the housing, and a dielectric fluid disposed within the housing. The artificial muscle is positioned such that the expandable fluid region is offset from a perimeter of the first plate and the second plate of the plate pair. The SMA wire is coupled to the plate pair such that application of a stimulant such as current flowing in the SMA wire contracts the SMA wire and closes the plate pair together, placing the hybrid actuation device in an actuated state. The SMA wire is disposed to pass through the dielectric fluid in the expandable fluid region so that the dielectric fluid cools the SMA wire. When the SMA wire contracts, drawing the plate pair together and placing the hybrid actuation device in the actuated state, the dielectric fluid is directed into the expandable fluid region, expanding the expandable fluid region. Moreover, the first and second electrode electrostatically attract upon application of a voltage to hold the hybrid actuation device in the actuated state. This allows actuation (e.g., contraction) of the SMA wire to cease while retaining the hybrid actuation device in the actuated state. The hybrid actuation device combines the actuation force achievable with an SMA wire and the displacement achievable with an artificial muscle to provide an improved actuation device. Various embodiments of the hybrid actuation device and the operation of which, are described in more detail herein. Whenever possible, the same reference numerals will be used throughout the drawings to refer to the same or like parts.

Figure 1B:
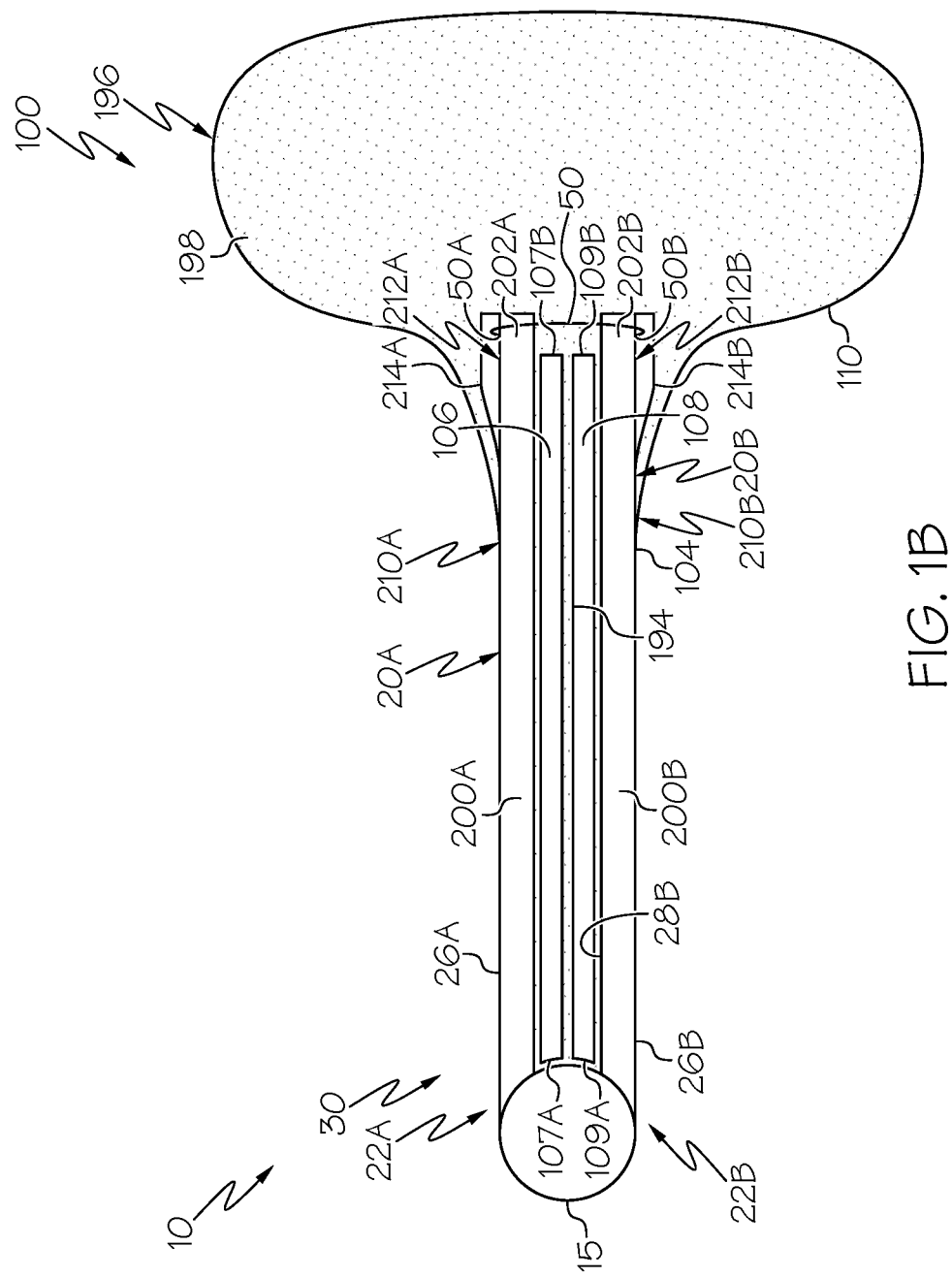
FIG. 1B schematically depicts a side view of the hybrid actuation device of FIG. 1A in an actuated state, according to one or more embodiments shown and described herein.

Referring now to FIGS. 1A and 1B, a hybrid actuation device 10 is schematically depicted in a non-actuated state (FIG. 1A) and an actuated state (FIG. 1B). The hybrid actuation device includes a first plate 20A coupled to a second plate 20B, for example, along a first end 22A, 22B of each plate 20A, 20B to form a plate pair 30. The first plate 20A and the second plate 20B each comprise a rigid material, such as a rigid polymer, metal, ceramic, or the like. One example rigid polymer is acrylic. The first plate 20A and the second plate 20B are coupled together in a manner facilitating rotational motion of the first plate 20A and the second plate 20B with respect to each other. For example, the first plate 20A and the second plate 20B may be coupled together by a hinge 15 along the first end 22A, 22B of each plate 20A, 20B to pivotally couple the first plate 20A to the second plate 20B. Each plate 20A, 20B also includes a second end 24A, 24B opposite the first end 22A, 22B and an outer surface 26A, 26B opposite an inner surface 28A, 28B. In addition, the first plate 20A and the second plate 20B each include a perimeter 25A, 25B, a central portion 200A, 200B, and an overhanging portion 202A, 202B. The central portion 200A of the first plate 20A may extend between the first end 22A and the overhanging portion 202A. The overhanging portion 202A may extend away from the central portion 200A. Similarly, the central portion 200B of the second plate 20B may extend between the first end 22B and the overhanging portion 202B. The overhanging portion 202B may extend away from the central portion 200B.

Referring still to FIGS. 1A and 1B, the hybrid actuation device 10 comprises at least one artificial muscle 100 positioned between the first plate 20A and the second plate 20B. The artificial muscle 100 includes an electrode pair 104 comprising a first electrode 106 and a second electrode 108 disposed in a housing 110 together with a dielectric fluid 198. A "dielectric" fluid as used herein is a medium or material that transmits electrical force without conduction and as such has low electrical conductivity. Some non-limiting example dielectric fluids include perfluoroalkanes, transformer oils, and deionized water.

The first electrode 106 may include a first end 107A and an opposite second end 107B. The first electrode 106 may be coupled to the first plate 20A at the central portion 200A such that the overhanging portion 202A extends away and is spaced apart from the second end 107B of the first electrode 106. The first end 107A of the first electrode 106 may be positioned adjacent the hinge 15 so that the first end 107A is closer to the hinge 15 than the second end 107B. Similarly, the second electrode 108 may include a first end 109A and an opposite second end 109B. The second electrode 108 may be coupled to the second plate 20B at the central portion 200B such that the overhanging portion 202B extends away and is spaced apart from the second end 109B of the second electrode 108. The first end 109A of the second electrode 108 may be positioned adjacent the hinge 15 so that the first end 109A is closer to the hinge 15 than the second end 109B.

The housing 110 may be coupled to the outer surface 26A of the first plate 20A at a first sealed region 210A and coupled to the outer surface 26B of the second plate 20B at a second sealed region 210B. The first sealed region 210A and the second sealed region 210B may be a region on the outer surface 26A of the first plate 20A and the outer surface 26B of the second plate 20B, respectively, where the housing 110 is at least partially heat sealed to the first plate 20A and the second plate 20B. Particularly, the first plate 20A and the second plate 20B may include an outer surface formed of biaxially oriented polypropylene that heat seals on contact with the housing 110 when the housing 110 is similarly formed of biaxially oriented polypropylene. In other embodiments, the outer surface of the first plate 20A and the second plate 20B may include an adhesive for sealing to the housing 110.

The hybrid actuation device 10 may further include a first protective film 214A and a second protective film 214B. The first protective film 214A may be positioned in a first unsealed region 212A adjacent the first sealed region 210A to prevent the housing 110 from heat sealing to the first plate 20A at the first unsealed region 212A. The first protective film 214A may be coupled to the first plate 20A to be positioned between the housing 110 and the first plate 20A. The first protective film 214A may be formed of any material suitable to prevent the housing 110 from heat sealing to the first plate 20A and second plate 20B, such as, for example, plastic. The second protective film 214B may be positioned in a second unsealed region 212B adjacent the second sealed region 210B to prevent the housing 110 from heat sealing to the second plate 20B at the second unsealed region 212B. The second protective film 214B may be coupled to the second plate 20B to be positioned between the housing 110 and the second plate 20B. The second protective film 214B may be formed of a similar material as the first protective film 214A to prevent heat sealing between the housing 110 and the second plate 20B at the second unsealed region 212B. The first unsealed region 212A and the second unsealed region 212B may be positioned coaxial with the expandable fluid region 196 at the overhanging portion 202A of the first plate 20A and the overhanging portion 202B of the second plate 20B to prevent the housing 110 from heat sealing to the SMA wire 50. By providing the SMA wire 50 in the first unsealed region 212A and the second unsealed region 212B, the first end 50A and the second end 50B of the SMA wire 50 may be positioned within the expandable fluid region 196 and submerged within the dielectric fluid 198. In embodiments, the hybrid actuation device 10 may not include the protective films 214A, 214B where the housing 110 may be allowed to heat seal to the first plate 20A and the second plate 20B over the SMA wires 50.

Figure 3:
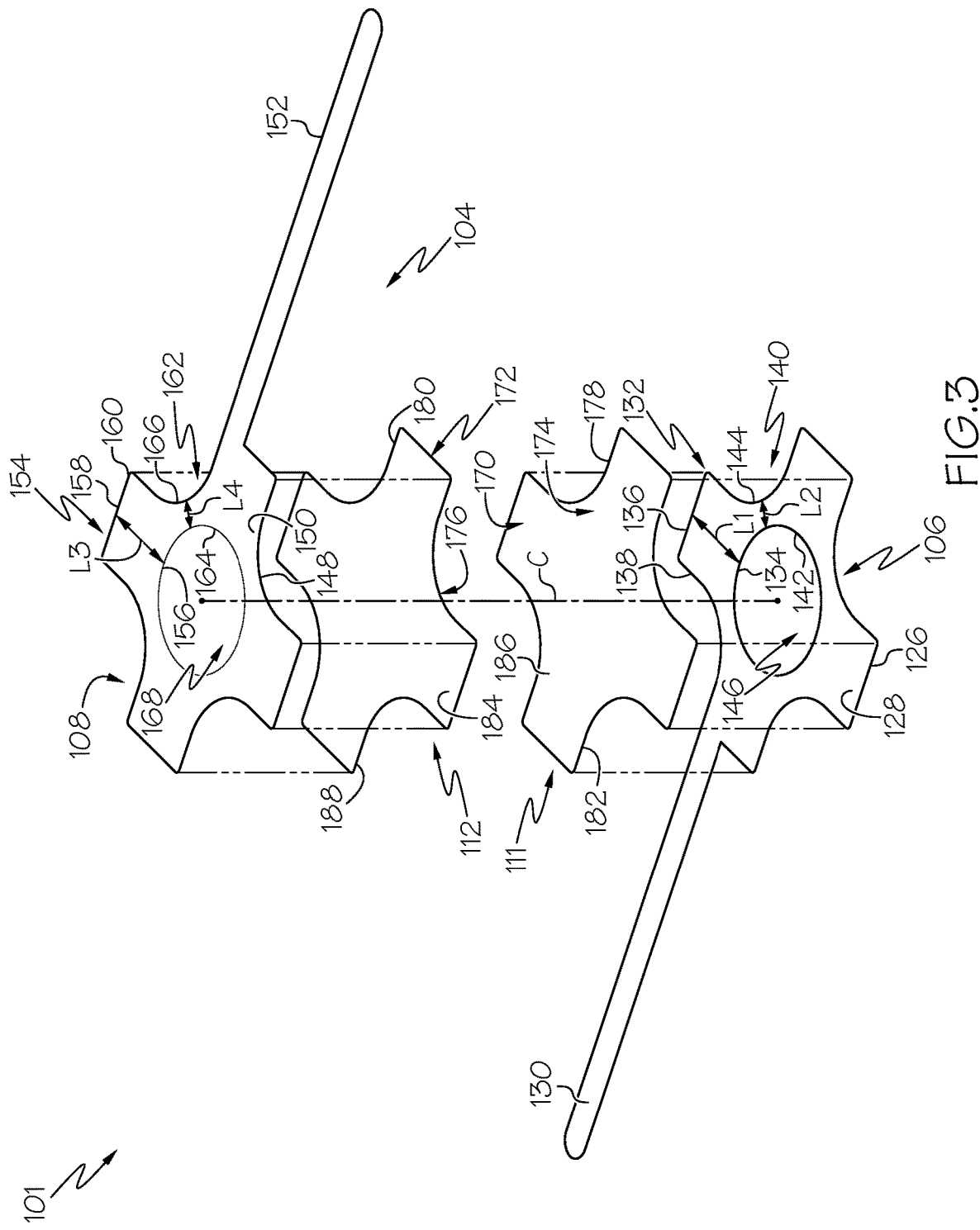
FIG. 3 schematically depicts an exploded view of an example artificial muscle, according to one or more embodiments shown and described herein.

The electrode pair 104 is disposed in an electrode region 194 of the housing 110, adjacent an expandable fluid region 196. In operation, voltage may be applied to the electrode pair 104, electrostatically attracting the electrode pair 104 together. For example, voltage may be applied by a power supply 430A (FIG. 10), which is electrically coupled to the electrode pair 104 by terminals 130, 152 (FIG. 3). Providing the voltage may comprise generating the voltage, for example, in an embodiment in which the power supply 430A (FIG. 10) is a battery, converting the voltage, for example in embodiment in which the power supply 430A (FIG. 10) is a power adaptor, or any other known or yet to be developed technique for readying a voltage for application. As depicted in FIGS. 1A and 1B, the expandable fluid region 196 of the housing 110 is positioned apart from a perimeter 25A, 25B of the first plate 20A and the second plate 20B. In FIGS. 1A and 1B, the expandable fluid region 196 is positioned apart from the second end 24A, 24B of the first plate 20A and the second plate 20B. Thus, the expandable fluid region 196 is not impeded from expanding when the first plate 20A and the second plate 20B are drawn together, as shown in FIG. 1B. As the housing 110 is coupled to the first plate 20A and the second plate 20B, electrostatic attraction between the first electrode 106 and the second electrode 108 holds the first plate 20A and the second plate 20B together, holding the hybrid actuation device 10 in the actuated state, as depicted in FIG. 1B. In some embodiments, the first electrode 106 and the second electrode 108 comprise a rectilinear shape. However, it should be understood that other shapes and designs are contemplated, for example, as shown by the example artificial muscles 101, 301, 301', described in more detail below with respect to FIGS. 3-9.

The hybrid actuation device 10 further comprises at least one SMA wire 50 that may extend between the first plate 20A and the second plate 20B. The SMA wire 50 may include a first end 50A and an opposite second end 50B. The first end 50A of the SMA wire 50 may be coupled to the outer surface 26A of the first plate 20A and extend through the first plate 20A at the overhanging portion 202A so that the SMA wire 50 is spaced apart from and does not contact the first electrode 106. Similarly, the second end 50B of the SMA wire 50 may be coupled to the outer surface 26B of the second plate 20B and extend through the second plate 20B at the overhanging portion 202B so that the SMA wire 50 is spaced apart from and does not contact the second electrode 108. The SMA wire 50 may be threaded through each of the first plate 20A and the second plate 20B to allow the ends 50A, 50B of the SMA wire 50 to be coupled to the outer surfaces 26A, 26B of the first plate 20A and the second plate 20B, respectively. However, it is contemplated and possible for the SMA wire 50 to be coupled to the inner surface 28A of the first plate 20A and/or the inner surface 28B of the second plate 20B at the overhanging portions 202A, 202B such that the SMA wire 50 is entirely disposed between the first plate 20A and the second plate 20B.

Each SMA wire 50 comprises a SMA material configured to contract in response to a stimulant, such as heat, current, or a magnetic field. For example, in embodiments where the SMA wire 50 is formed of a SMA material that contacts in response to heat or current that increases the temperature of the SMA wire 50, the SMA wire 50 contracts when the SMA material passes a threshold temperature. In embodiments, the SMA wire 50 contracts when subjected to temperatures between 40° F. and 200° F. In embodiments, the SMA wire 50 contracts when subjected to temperatures between 80° F. and 150° F. In embodiments, the SMA wire 50 contracts when subjected to temperatures between 100° F. and 120° F. In operation, a stimulant, such as the inducement of current flow within the SMA wire 50 may be applied by a power supply 430B (FIG. 10), which is electrically coupled to each SMA wire 50. Without intending to be limited by theory, in some embodiments, the power supply 430B may generate a higher amperage and a lower voltage than the power supply 430A as the SMA wire 50 is actuated by current and the electrode pair 104 is electrostatically attracted by voltage. In operation, applying the stimulant to each SMA wire 50 contracts each SMA wire 50 and draws the first plate 20A and the second plate 20B together. Drawing the first plate 20A and the second plate 20B together moves the hybrid actuation device 10 from the non-actuated state, as shown in FIG. 1A, to the actuated state, as shown in FIG. 1B. The SMA wire 50 may comprise (i) silver-cadmium, (ii) gold-cadmium, (iii) cobalt-nickel-aluminum, (iv) cobalt-nickel-gallium, (v) copper-aluminum-beryllium and at least one of zirconium, boron, chromium, or gadolinium, (vi) copper-aluminum-nickel, (vii) copper-aluminum-nickel-hafnium, (viii) copper-tin, (ix) copper-zinc, (x) copper-zinc and at least one of silicon, aluminum, or tin, (xi) iron-manganese-silicon, (xii) iron-platinum, (xiii) manganese-copper, (xiv) nickel-iron-gallium (xv) nickel-titanium, (xvi) nickel-titanium-hafnium, (xvii) nickel-titanium-palladium, (xviii) nickel-manganese-gallium, (xix) titanium-niobium, or any combination thereof.

Referring still to FIGS. 1A and 1B, actuating the hybrid actuation device 10 comprises stimulating the SMA wire 50 to raise the temperature of the SMA wire 50 in excess of the threshold temperature to contract the SMA wire 50 and draw the first plate 20A and the second plate 20B together. This places the hybrid actuation device 10 in an-actuated state as depicted in FIG. 1B. Stimulating the SMA wire 50 comprises directing a current through the SMA wire 50, heating the SMA wire 50, and/or applying a magnetic field to the SMA wire 50. When the first plate 20A and the second plate 20B are drawn together, dielectric fluid 198 disposed in the electrode region 194 of the housing 110 is directed into the expandable fluid region 196, thereby expanding the expandable fluid region 196. Next, the voltage may be applied to the electrode pair 104, electrostatically attracting the first electrode 106 and the second electrode 108 together to hold the hybrid actuation device 10 in the actuated state. Once the electrode pair 104 is drawn together by voltage application, the stimulant may be removed from the SMA wire 50. When the stimulant is removed from the SMA wire 50, the SMA wire 50 cools to a temperature that is below the threshold temperature. When below the threshold temperature, a length of the SMA wire 50 increases. The submersion of the SMA wire 50 within the dielectric fluid 198 reduces the time required for the SMA wire 50 to cool to a temperature below the threshold temperature.

The continued application of voltage to the electrode pair 104 retains the hybrid actuation device 10 in the actuated state. Thus, the electrostatic attraction of the electrode pair 104 may retain the hybrid actuation device 10 in the actuated state without the negative thermal buildup of prolonged actuation of the SMA wire 50.

In operation, when the hybrid actuation device 10, 10's actuated by contracting the SMA wire 50, expansion of the expandable fluid region 196 produces a force of 25 Newton-millimeters (N·mm) per cubic centimeter ($cm^3$) of actuator volume or greater, such as 30 N·mm per $cm^3$ or greater, 35 N·mm per $cm^3$ or greater, 40 N·mm per $cm^3$ or greater, 45 N·mm per $cm^3$ or greater, 50 N·mm per $cm^3$ or greater, 55 N·mm per $cm^3$ or greater, 60 N·mm per $cm^3$ or greater, 70 N·mm per $cm^3$ or greater, 80 N·mm per $cm^3$ or greater, 90 N·mm per $cm^3$ or greater, 100 N·mm per $cm^3$ or greater, 125 N·mm per $cm^3$ or greater, or any value within a range having any two of these values as endpoints. In one example, the hybrid actuation device 10, 10', may be actuated to lift a weight of 10.5 kilograms a displacement distance of 1 mm. It should be understood that increasing displacement distances are contemplated, such as 1.5 mm or greater, 2 mm or greater, 5 mm or greater, 10 mm or greater, or any value within a range having any two of these values as endpoints.

Figure 2:
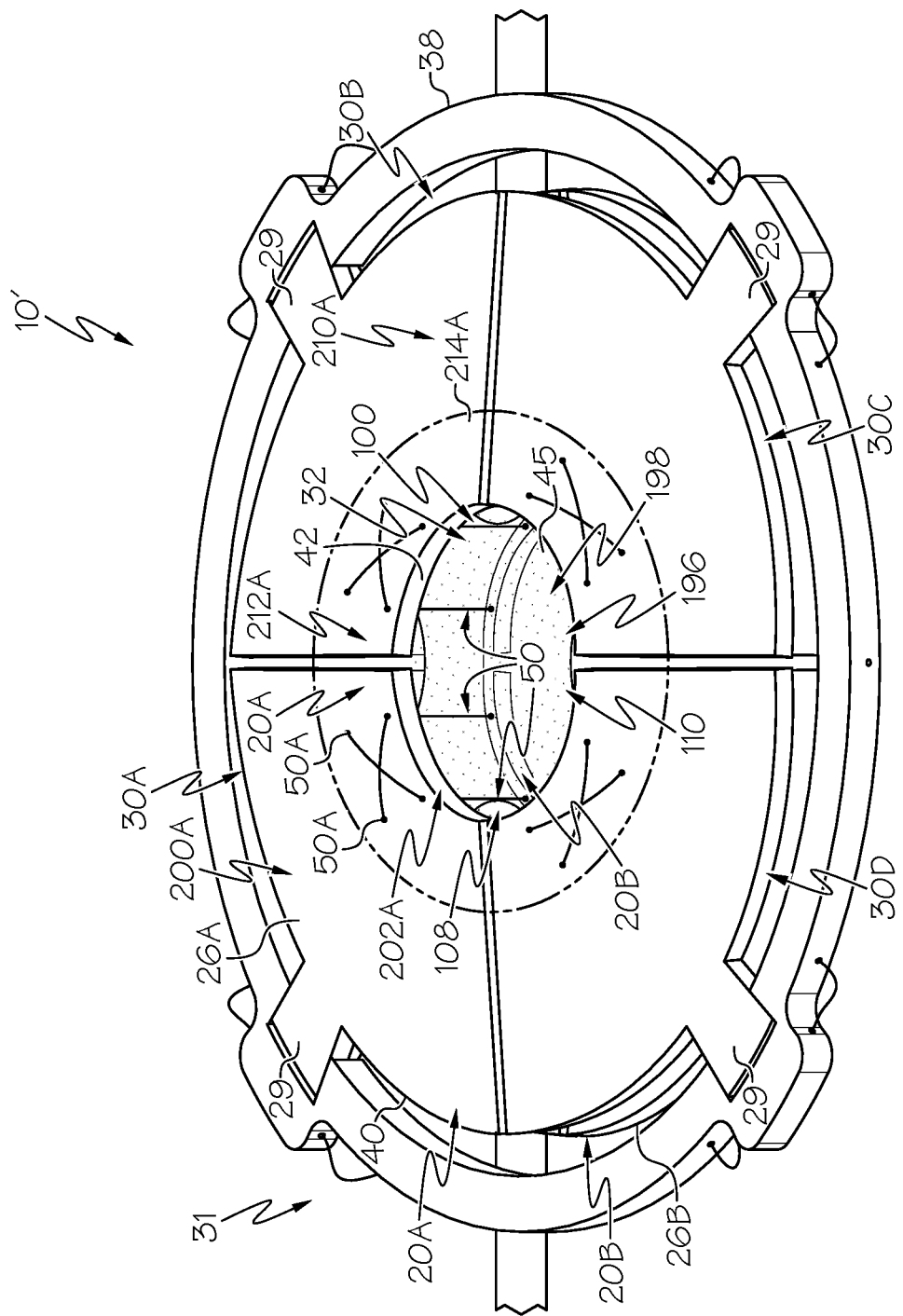
FIG. 2 schematically depicts a perspective view of a hybrid actuation device having a plurality of plate pairs arranged in an annular plate system in a non-actuated state, according to one or more embodiments shown and described herein.

Referring now to FIG. 2, a hybrid actuation device 10' is depicted that comprises a plurality of plate pairs 30. In the hybrid actuation device 10', the first plate 20A and the second plate 20B of each of the plurality of plate pairs 30 may be arranged to form a plate system 31 comprising an opening 32 positioned in a central region of the plate system 31. In embodiments, the plurality of plate pairs 30 may have an annular sector shape such that the plurality of plate pairs 30 form an annular plate system 31 with the opening 32 positioned in the central region of the annular plate system 31. The hybrid actuation device 10' is depicted in the non-actuated state. The opening 32 is bounded by the second end 24A, 24B of the first and second plate 20A, 20B of each of the plurality of plate pairs 30. The expandable fluid region 196 of the artificial muscle 100 is positioned in the opening 32 of the annular plate system 31 such that expansion of the expandable fluid region 196 is not impeded by actuation of the hybrid actuation device 10'. In other words, the opening 32 of the annular plate system 31 may encircle the expandable fluid region 196. Because the first plate 20A and the second plate 20B of each of the plurality of plate pairs 30 is an annular sector shape, the first end 22A, 22B of the first and second plates 20A, 20B comprises an outer curved edge 40 and the second end 24A, 24B of the first and second plates 20A, 20B comprises an inner curved edge 42. In the embodiment depicted in FIG. 2, the annular plate system 31 comprises four plate pairs 30A, 30B, 30C, and 30D. However, it should be understood that the annular plate system 31 may comprise any number of plate pairs 30 arranged in a collective annular shape.

In FIG. 2, the first plate 20A and the second plate 20B of each of the plurality of plate pairs 30 are coupled together along their respective outer curved edges 40. For example, the first plate 20A and the second plate 20B of each of the plurality of plate pairs 30 are coupled together in a hinged connection along their respective outer curved edges 40. In some embodiments, the hybrid actuation device 10' includes an outer ring 38 surrounding the outer curved edges 40 of the plurality of plate pairs 30. The outer ring 38 provides a location for the hinged connection between first and second plates 20A, 20B of the respective plate pairs 30. Indeed, in the embodiments of FIG. 2, the outer curved edges 40 of the first and second plates 20A, 20B have an extended region 29 extending radially outward toward the outer ring 38 and the hinged connection is located at the connection point between the outer ring 38 and the extended regions 29. Moreover, the arc length of the extended region 29 is less than the arc length of the outer curved edge 40, for example, from 10% to 40% of the arc length of the outer curved edge 40. This forms a gap between the outer ring 38 and a portion of the outer curved edges 40 of the plate pairs 30.

Referring now to FIG. 2, the hybrid actuation device 10' comprises a plurality of SMA wires 50 coupled to the plurality of plate pairs 30 of the annular plate system 31. In FIG. 2, the housing 110 is hidden from view to better illustrate the internal components of the device 10'. However, the housing 110 may extend around each of the plurality of plate pairs 30 to envelop the annular plate system 31. Each of the plurality of plate pairs 30 may include SMA wires 50 disposed such that the SMA wires 50 form a cross pattern on the outer surface 26A of the first plate 20A. The SMA wires 50 are coupled to the outer surface 26A of the first plate 20A at the respective first ends 50A of the SMA wires 50 and cross over one another to form the cross pattern. The SMA wires 50 then extend from the outer surface 26A through the first plate 20A to extend to the second plate 20B. The SMA wires 50 may similarly extend through the second plate 20B and form a cross pattern on the outer surface 26B of the second plate 20B with the second ends 50B of the SMA wires 50 being coupled to the outer surface 26B of the second plate 20B. The SMA wires 50 extend between the first plate 20A and the second plate 20B such that the SMA wires 50 extend through the dielectric fluid 198. The first protective film 214A (shown in phantom) may be positioned to extend across the opening 32 between the first plates 20A of each of the plurality of plate pairs 30. As discussed above, the first protective film 214A is positioned in the first unsealed region 212A to cover the first end 50A of each of the SMA wires 50. The annular plate system 31 may similarly include a second opening (not shown) disposed opposite the opening 32 that is surrounded by the second plates 20B of the plurality of plate pairs 30. The second protective film 214B (FIG. 5) may be disposed to extend across the second opening between the second plates 20B of each of the plurality of plate pairs 30. While FIG. 2 depicts two SMA wires 50 extending between each of the plate pairs 30, the hybrid actuation device 10 may include any operable number of SMA wires 50 for moving the plate pairs 30 together, such as one, two, three, four, or more than four.

Referring to FIGS. 3-9, example artificial muscles 101 (FIGS. 3-6), 301 (FIGS. 7 and 8), and 301' (FIG. 9) are depicted. These artificial muscles 101, 301, 301' are examples that may be used as the artificial muscle 100 in the hybrid actuation device 10 of FIGS. 1A-2. Moreover, it should be understood that these are merely some examples of the artificial muscle 100 that may be used in the hybrid actuation device 10. It should further be understood that artificial muscles 101, 301, 301' include additional components beyond those depicted by the artificial muscle 100 shown in FIGS. 1A-2 and may be incorporated into the artificial muscle 100.

Figure 4:
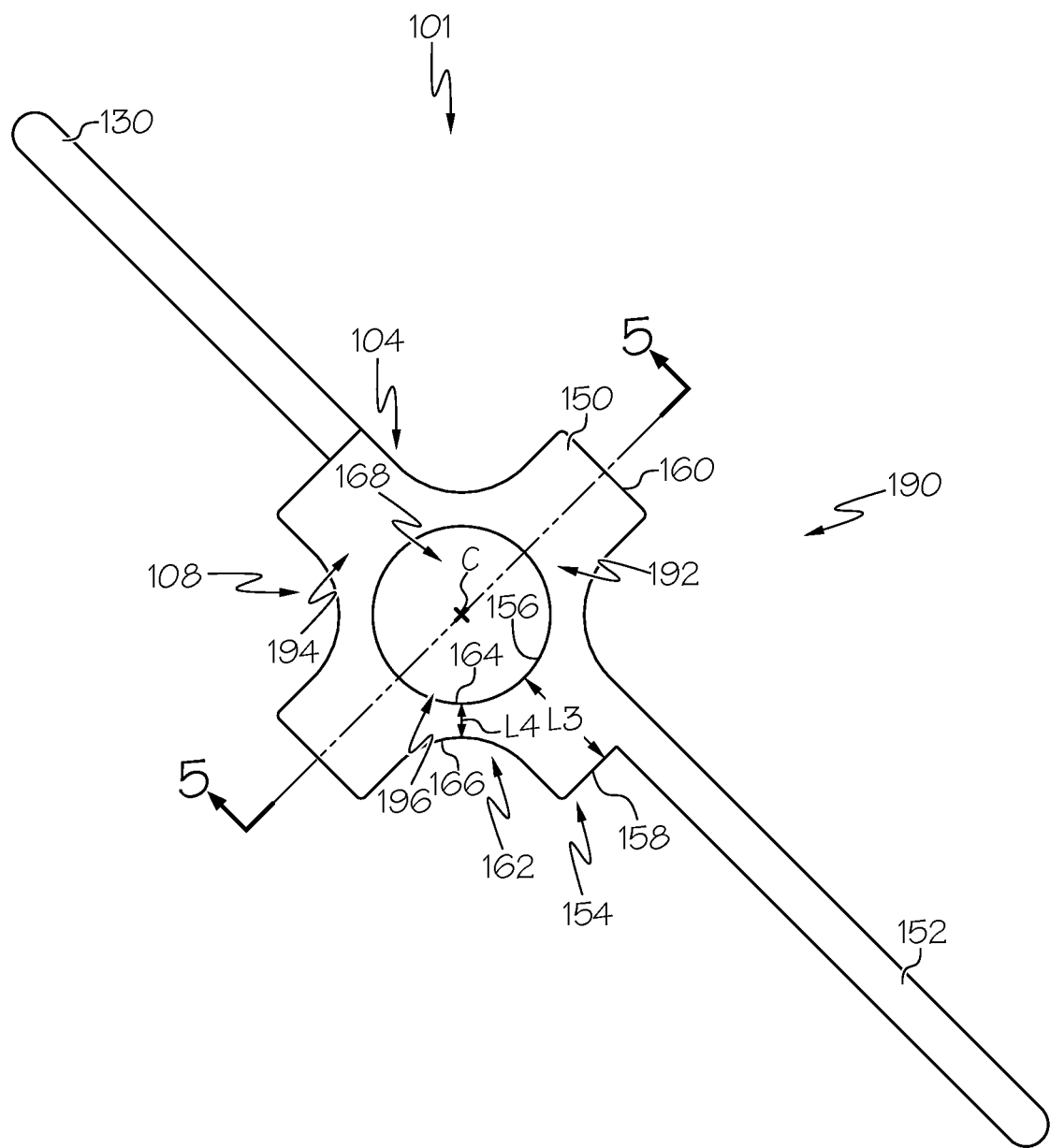
FIG. 4 schematically depicts a top view of the artificial muscle of FIG. 3 in an assembled state, according to one or more embodiments shown and described herein.

Referring now to FIGS. 3 and 4, the first electrode 106 and the second electrode 108 may each be formed of aluminum-coated polyester such as, for example, Mylar®.

In addition, one of the first electrode 106 and the second electrode 108 is a negatively charged electrode and the other of the first electrode 106 and the second electrode 108 is a positively charged electrode. For purposes discussed herein, either electrode 106, 108 may be positively charged so long as the other electrode 106, 108 of the artificial muscle 101 is negatively charged.

Figure 10:
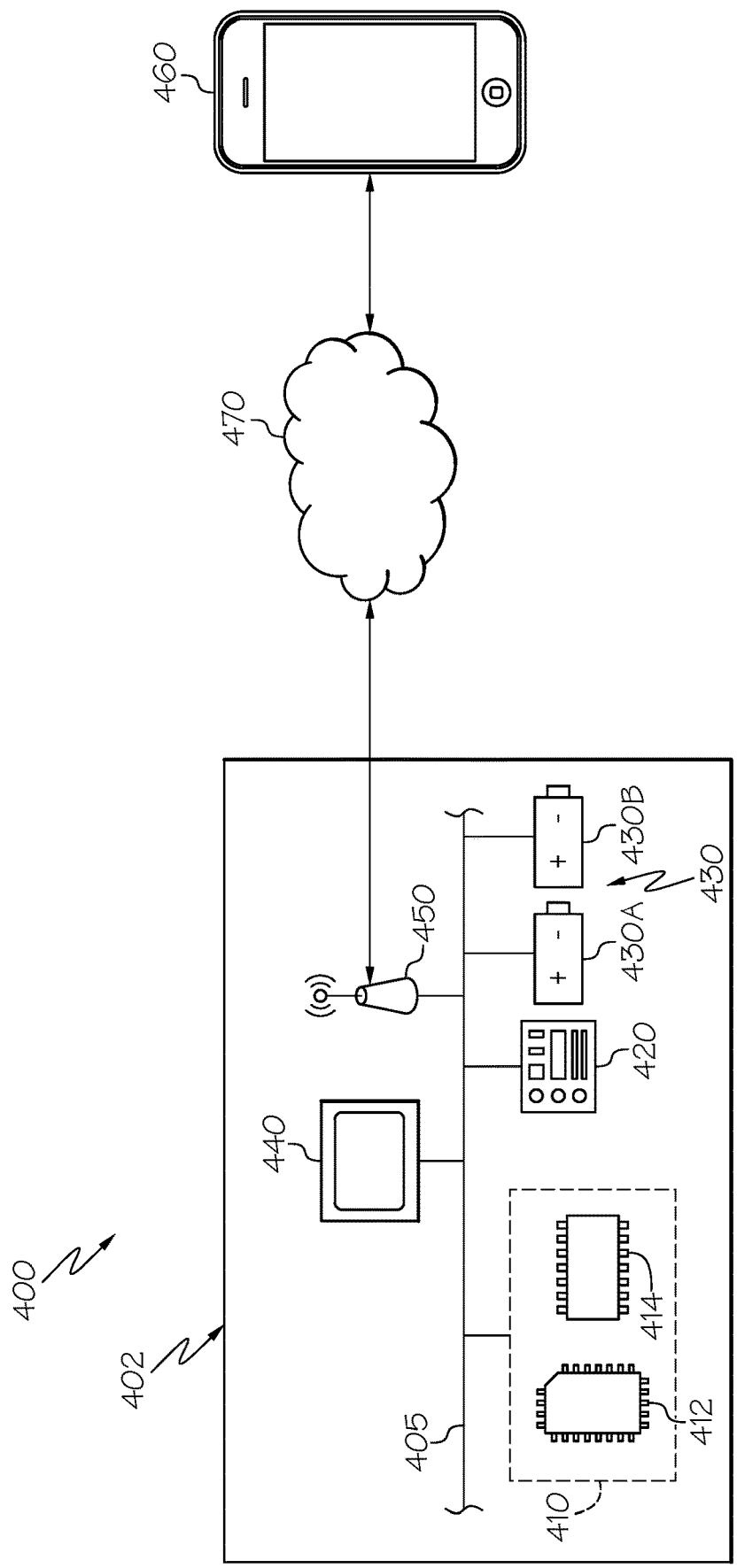
FIG. 10 schematically depicts an actuation system for operating the hybrid actuation device of FIGS. 1A-2, according to one or more embodiments shown and described herein.

The first electrode 106 may have a film-facing surface 126 and an opposite inner surface 128. In addition, the first electrode 106 may include the first terminal 130 extending from the first electrode 106 such that the first terminal 130 can be connected to a power supply to actuate the first electrode 106. Specifically, the terminal 130 may be coupled, either directly or in series, to a power supply and a controller of an actuation system 400, as shown in FIG. 10. Similarly, the second electrode 108 may have a film-facing surface 148 and an opposite inner surface 150. The second electrode 108 may include the second terminal 152 extending from the second electrode 108 such that the second terminal 152 can be connected to a power supply and a controller of the actuation system 400 to actuate the second electrode 108.

In embodiments, the first electrode 106 includes two or more tab portions 132 and two or more bridge portions 140. Each bridge portion 140 is positioned between adjacent tab portions 132, interconnecting these adjacent tab portions 132. Each tab portion 132 has a first end 134 extending radially from a center axis C of the first electrode 106 to an opposite second end 136 of the tab portion 132, where the second end 136 defines a portion of an outer perimeter 138 of the first electrode 106. Each bridge portion 140 has a first end 142 extending radially from the center axis C of the first electrode 106 to an opposite second end 144 of the bridge portion 140 defining another portion of the outer perimeter 138 of the first electrode 106. Each tab portion 132 has a tab length L1 and each bridge portion 140 has a bridge length L2 extending in a radial direction from the center axis C of the first electrode 106. The tab length L1 is a distance from the first end 134 to the second end 136 of the tab portion 132 and the bridge length L2 is a distance from the first end 142 to the second end 144 of the bridge portion 140. The tab length L1 of each tab portion 132 is longer than the bridge length L2 of each bridge portion 140. In some embodiments, the bridge length L2 is 20% to 50% of the tab length L1, such as 30% to 40% of the tab length L1.

In some embodiments, the two or more tab portions 132 are arranged in one or more pairs of tab portions 132. Each pair of tab portions 132 includes two tab portions 132 arranged diametrically opposed to one another. In some embodiments, the first electrode 106 may include only two tab portions 132 positioned on opposite sides or ends of the first electrode 106. In some embodiments, as shown in FIGS. 3 and 4, the first electrode 106 includes four tab portions 132 and four bridge portions 140 interconnecting adjacent tab portions 132. In this embodiment, the four tab portions 132 are arranged as two pairs of tab portions 132 diametrically opposed to one another. Furthermore, as shown, the first terminal 130 extends from the second end 136 of one of the tab portions 132 and is integrally formed therewith.

Like the first electrode 106, the second electrode 108 may include at least a pair of tab portions 154 and two or more bridge portions 162. Each bridge portion 162 is positioned between adjacent tab portions 154, interconnecting these adjacent tab portions 154. Each tab portion 154 has a first end 156 extending radially from a center axis C of the second electrode 108 to an opposite second end 158 of the tab portion 154, where the second end 158 defines a portion of an outer perimeter 160 of the second electrode 108. Due to the first electrode 106 and the second electrode 108 being coaxial with one another, the center axis C of the first electrode 106 and the second electrode 108 are the same. Each bridge portion 162 has a first end 164 extending radially from the center axis C of the second electrode to an opposite second end 166 of the bridge portion 162 defining another portion of the outer perimeter 160 of the second electrode 108. Each tab portion 154 has a tab length L3 and each bridge portion 162 has a bridge length L4 extending in a radial direction from the center axis C of the second electrode 108. The tab length L3 is a distance from the first end 156 to the second end 158 of the tab portion 154 and the bridge length L4 is a distance from the first end 164 to the second end 166 of the bridge portion 162. The tab length L3 is longer than the bridge length L4 of each bridge portion 162. In some embodiments, the bridge length L4 is 20% to 50% of the tab length L3, such as 30% to 40% of the tab length L3.

In some embodiments, the two or more tab portions 154 are arranged in one or more pairs of tab portions 154. Each pair of tab portions 154 includes two tab portions 154 arranged diametrically opposed to one another. In some embodiments, the second electrode 108 may include only two tab portions 154 positioned on opposite sides or ends of the first electrode 106. In some embodiments, as shown in FIGS. 3 and 4, the second electrode 108 includes four tab portions 154 and four bridge portions 162 interconnecting adjacent tab portions 154. In this embodiment, the four tab portions 154 are arranged as two pairs of tab portions 154 diametrically opposed to one another. Furthermore, as shown, the second terminal 152 extends from the second end 158 of one of the tab portions 154 and is integrally formed therewith.

At least one of the first electrode 106 and the second electrode 108 has a central opening formed therein between the first end 134 of the tab portions 132 and the first end 142 of the bridge portions 140. As depicted in FIGS. 3 and 4, the first electrode 106 has a central opening 146 and the second electrode 108 has a central opening 168. However, it should be understood that the first electrode 106 does not need to include the central opening 146 when a central opening is provided within the second electrode 108. Alternatively, the second electrode 108 does not need to include the central opening when the central opening 146 is provided within the first electrode 106.

As shown in FIG. 4, the second electrode 108 is stacked on top of the first electrode 106 and, therefore, the first electrode 106 is not shown. The first terminal 130 of the first electrode 106 and the second terminal 152 of the second electrode 108 extend past an outer perimeter of the housing 110.

Referring still to FIGS. 3 and 4, the artificial muscles 101 also includes a first electrical insulator layer 111 fixed to the first electrode 106, and a second electrical insulator layer 112 fixed to the second electrode 108. The first electrical insulator layer 111 and the second electrical insulator layer 112 may have a geometry generally corresponding to the first electrode 106 and the second electrode 108, respectively. Thus, the first electrical insulator layer 111 and the second electrical insulator layer 112 each have tab portions 170, 172 and bridge portions 174, 176 corresponding to like portions on the first electrode 106 and the second electrode 108. Further, the first electrical insulator layer 111 and the second electrical insulator layer 112 each have an outer perimeter 178, 180 corresponding to the outer perimeter 138 of the first electrode 106 and the outer perimeter 160 of the second electrode 108, respectively, when positioned thereon.

It should be appreciated that, in some embodiments, the first electrical insulator layer 111 and the second electrical insulator layer 112 generally include the same structure and composition. As such, in some embodiments, the first electrical insulator layer 111 and the second electrical insulator layer 112 each include an adhesive surface 182, 184 and an opposite non-sealable surface 186, 188, respectively. Thus, in some embodiments, the first electrical insulator layer 111 and the second electrical insulator layer 112 are each a polymer tape adhered to the inner surface 128 of the first electrode 106 and the inner surface 150 of the second electrode 108, respectively.

Figure 5:
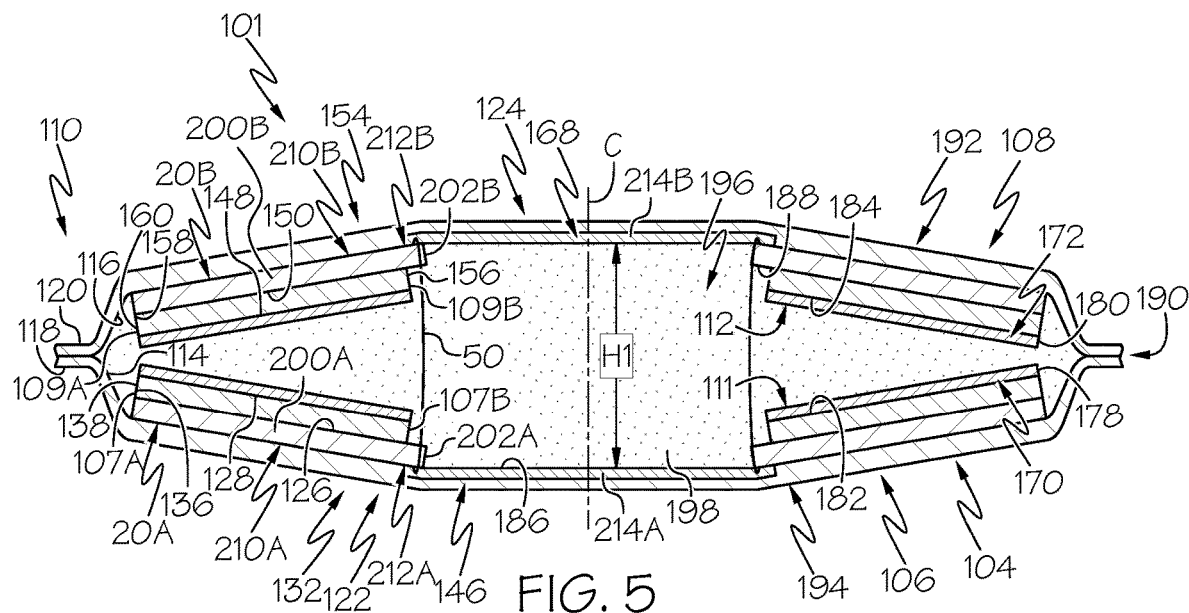
FIG. 5 schematically depicts a cross-sectional view of the artificial muscle of FIG. 3 taken along line 5-5 in FIG. 4 in a non-actuated state, according to one or more embodiments shown and described herein.
Figure 6:
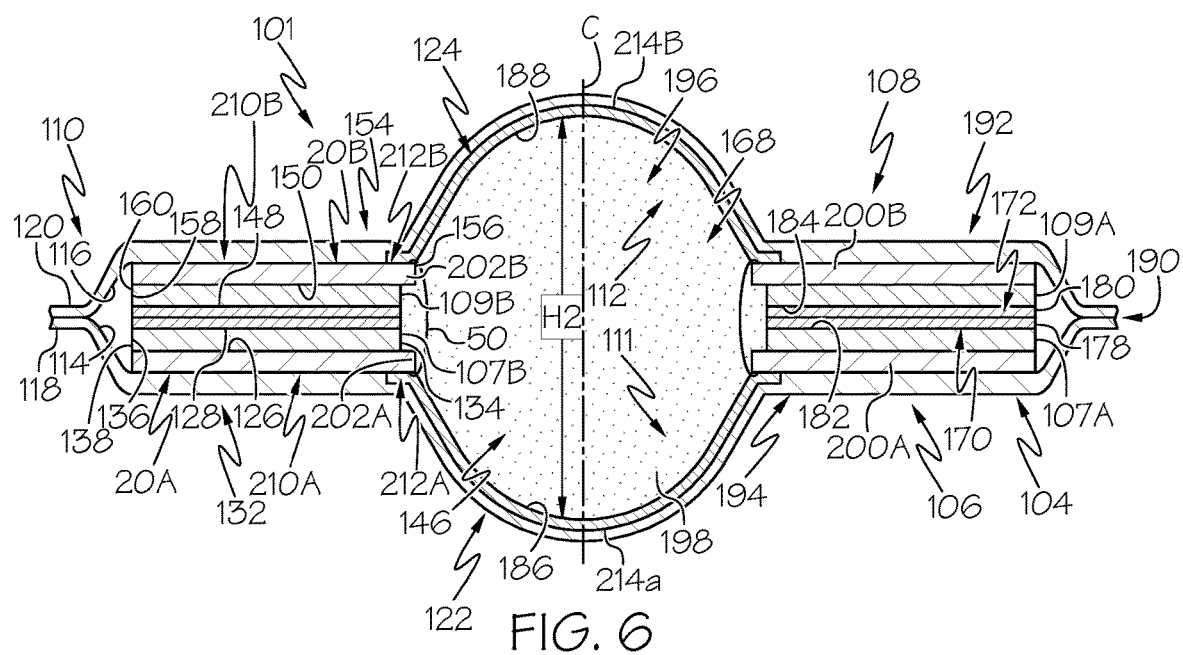
FIG. 6 schematically depicts a cross-sectional view of the artificial muscle of FIG. 3 taken along line 5-5 in FIG. 4 in an actuated state, according to one or more embodiments shown and described herein.

Referring now to FIGS. 5 and 6, the housing 110 may be a one-piece monolithic layer including a pair of opposite inner surfaces, such as a first inner surface 114 and a second inner surface 116, and a pair of opposite outer surfaces, such as a first outer surface 118 and a second outer surface 120. In some embodiments, the first inner surface 114 and the second inner surface 116 of the housing 110 are heat-sealable. In other embodiments, the housing 110 may be a pair of individually fabricated film layers, such as a first film layer 122 and a second film layer 124. Thus, the first film layer 122 includes the first inner surface 114 and the first outer surface 118, and the second film layer 124 includes the second inner surface 116 and the second outer surface 120.

While the embodiments described herein primarily refer to the housing 110 as comprising the first film layer 122 and the second film layer 124, as opposed to the one-piece housing, it should be understood that either arrangement is contemplated. In some embodiments, the first film layer 122 and the second film layer 124 generally include the same structure and composition. For example, in some embodiments, the first film layer 122 and the second film layer 124 each comprises biaxially oriented polypropylene. Moreover, the housing 110 may comprise additional film layers. For example, both the first film layer 122 and the second film layer 124 may include multiple layers of material.

Referring still to FIGS. 5 and 6, the first protective film 214A may be positioned between the first film layer 122 and the first plate 20A at the first unsealed region 212A to prevent the first film layer 122 from heat sealing to the first plate 20A at the first unsealed region 212A. The first film layer 122 may heat seal to the first plate 20A at the first sealed region 210A. The first protective film 214A may be fixedly coupled to the first plate 20A at the first unsealed region 212A and positioned in contact with the first film layer 122 such that the first protective film 214A expands and contracts with the first film layer 122. The second protective film 214B may similarly be positioned between the second film layer 124 and the second plate 20B to prevent the second film layer 124 from heat sealing to the second plate 20B at the second unsealed region 212B. The second film layer 124 may heat seal to the second plate 20B at the second sealed region 210B. The second protective film 214B may be fixedly coupled to the second plate 20B at the second unsealed region 212B and positioned in contact with the second film layer 124 such that the second protective film 214B expands and contracts with the second film layer 124.

Referring still to FIGS. 5 and 6, the first electrode 106 may be coupled to the first plate 20A and the second electrode 108 may be coupled to the second plate 20B. The first electrode 106 and the second electrode 108 may be coupled to the first plate 20A and the second plate 20B, respectively, such that they are fixed to the first plate 20A and the second plate 20B. The first electrode 106 may be coupled to the inner surface 28A of the first plate 20A at the central portion 200A such that the overhanging portion 202A extends away from and is positioned apart from second end 107B of the first electrode 106. The second electrode 108 may be coupled to the inner surface 28B of the second plate 20B at the central portion 200B such that the overhanging portion 202B extends away from and is positioned apart from the second end 109B of the second electrode 108. The first plate 20A, the second plate 20B, the first electrode 106, and the second electrode 108 are each positioned between the first film layer 122 and the second film layer 124.

The film-facing surface 126 of the first electrode 106 is coupled to the first plate 20A with the first plate 20A positioned against the first film layer 122, specifically, the first inner surface 114 of the first film layer 122, such that the first plate 20A is positioned between the first electrode 106 and the first film layer 122. The film-facing surface 148 of the second electrode 108 is coupled to the second plate 20B with the second plate 20B positioned against the second film layer 124, specifically, the second inner surface 116 of the second film layer 124, such that the second plate 20B is positioned between the second electrode 108 and the second film layer 124. Each of the central opening 146 of the first electrode 106 and the central opening 168 of the second electrode 108 may be positioned to encircle the expandable fluid region 196. The first protective film 214A may extend across the central opening 146 between the first film layer 122 and the dielectric fluid 198 in the expandable fluid region 196. The second protective film 214B may similarly extend across the central opening 168 in the second plate 20B between the second film layer 124 and the dielectric fluid 198 in the expandable fluid region 196.

In its assembled form, the first plate 20A, the second plate 20B, the first electrode 106, the second electrode 108, the first electrical insulator layer 111, and the second electrical insulator layer 112 are sandwiched between the first film layer 122 and the second film layer 124. The first film layer 122 is partially sealed to the second film layer 124 at an area surrounding the outer perimeter 138 of the first electrode 106 and the outer perimeter 160 of the second electrode 108. In some embodiments, the first film layer 122 is heat-sealed to the second film layer 124. Specifically, in some embodiments, the first film layer 122 is sealed to the second film layer 124 to define a sealed portion 190 surrounding the first electrode 106 and the second electrode 108. The first film layer 122 and the second film layer 124 may be sealed in any suitable manner, such as using an adhesive, heat sealing, or the like. The first film layer 122 is additionally heat-sealed to the first plate 20A at the first sealed region 210A, and the second film layer 124 is heat-sealed to the second plate 20B at the second sealed region 210B. The first protective film 214A is positioned between the first film layer 122 and the first plate 20A at the first unsealed region 212A, and the second protective film 214B is positioned between the second film layer 124 and the second plate 20B at the second unsealed region 212B.

The first electrode 106, the second electrode 108, the first electrical insulator layer 111, and the second electrical insulator layer 112 provide a barrier that prevents the first film layer 122 from sealing to the second film layer 124 forming an unsealed portion 192. The unsealed portion 192 of the housing 110 includes the electrode region 194, in which the electrode pair 104 is provided, and the expandable fluid region 196, which is surrounded by the electrode region 194. The central openings 146, 168 of the first electrode 106 and the second electrode 108 form the expandable fluid region 196 and are arranged to be axially stacked on one another. The housing 110 may be cut to conform to the geometry of the electrode pair 104 and reduce the size of the artificial muscle 101, namely, the size of the sealed portion 190. The dielectric fluid 198 is provided within the unsealed portion 192 and flows freely between the first electrode 106 and the second electrode 108. It should be appreciated that the dielectric fluid 198 may be injected into the unsealed portion 192 of the artificial muscle 101 using a needle or other suitable injection device.

Referring still to FIGS. 5 and 6, the artificial muscle 101 is actuatable between a non-actuated state and an actuated state. In the non-actuated state (FIG. 5), the first electrode 106 and the second electrode 108 are partially spaced apart from one another proximate the central openings 146, 168 thereof and the first end 134, 156 of the tab portions 132, 154. The second end 136, 158 of the tab portions 132, 154 remain in position relative to one another due to the housing 110 being sealed at the outer perimeter 138 of the first electrode 106 and the outer perimeter 160 of the second electrode 108. In the actuated state, as shown in FIG. 6, the first electrode 106 and the second electrode 108 are brought into contact with and oriented parallel to one another to force the dielectric fluid 198 into the expandable fluid region 196. This causes the dielectric fluid 198 to flow through the central openings 146, 168 of the first electrode 106 and the second electrode 108 and inflate the expandable fluid region 196.

Referring now to FIG. 5, the artificial muscle 101 is shown in the non-actuated state. The electrode pair 104 is provided within the electrode region 194 of the unsealed portion 192 of the housing 110. The central opening 146 of the first electrode 106 and the central opening 168 of the second electrode 108 are coaxially aligned within the expandable fluid region 196. In the non-actuated state, the first electrode 106 and the second electrode 108 are partially spaced apart from and non-parallel to one another. Due to the first film layer 122 being sealed to the second film layer 124 around the electrode pair 104, the second end 136, 158 of the tab portions 132, 154 are brought into contact with one another. Thus, dielectric fluid 198 is provided between the first electrode 106 and the second electrode 108, thereby separating the first end 134, 156 of the tab portions 132, 154 proximate the expandable fluid region 196. Stated another way, a distance between the first end 134 of the tab portion 132 of the first electrode 106 and the first end 156 of the tab portion 154 of the second electrode 108 is greater than a distance between the second end 136 of the tab portion 132 of the first electrode 106 and the second end 158 of the tab portion 154 of the second electrode 108. This results in the electrode pair 104 zippering toward the expandable fluid region 196 when actuated. In some embodiments, the first electrode 106 and the second electrode 108 may be flexible. Thus, as shown in FIG. 5, the first electrode 106 and the second electrode 108 are convex such that the second ends 136, 158 of the tab portions 132, 154 thereof may remain close to one another, but spaced apart from one another proximate the central openings 146, 168. In the non-actuated state, the expandable fluid region 196 has a first height H1.

When actuated, as shown in FIG. 6, the first electrode 106 and the second electrode 108 zipper toward one another from the second ends 144, 158 of the tab portions 132, 154 thereof, thereby pushing the dielectric fluid 198 into the expandable fluid region 196. As shown, when in the actuated state, the first electrode 106 and the second electrode 108 are parallel to one another. In the actuated state, the dielectric fluid 198 flows into the expandable fluid region 196 to inflate the expandable fluid region 196. As such, the first film layer 122 and the second film layer 124 expand in opposite directions. In the actuated state, the expandable fluid region 196 has a second height H2, which is greater than the first height H1 of the expandable fluid region 196 when in the non-actuated state. Although not shown, it should be noted that the electrode pair 104 may be partially actuated to a position between the non-actuated state and the actuated state. This would allow for partial inflation of the expandable fluid region 196 and adjustments when necessary.

In order to move the first electrode 106 and the second electrode 108 toward one another or to electrostatically hold the first electrode 106 and the second electrode 108 together, a voltage is applied by a power supply (such as power supply 430A of FIG. 10). In some embodiments, a voltage of up to 10 kV may be provided from the power supply to induce an electric field through the dielectric fluid 198. The resulting attraction between the first electrode 106 and the second electrode 108 pushes the dielectric fluid 198 into the expandable fluid region 196. Pressure from the dielectric fluid 198 within the expandable fluid region 196 causes the first film layer 122 and the first protective film 214A to deform in a first axial direction along the center axis C of the first electrode 106 and causes the second film layer 124 and the second protective film 214B to deform in an opposite second axial direction along the center axis C of the second electrode 108. Once the voltage being supplied to the first electrode 106 and the second electrode 108 is discontinued, the first electrode 106 and the second electrode 108 return to their initial, non-parallel position in the non-actuated state.

It should be appreciated that the present embodiments of the artificial muscle 101 disclosed herein, specifically, the tab portions 132, 154 with the interconnecting bridge portions 174, 176, provide a number of improvements over actuators that do not include the tab portions 132, 154, such as hydraulically amplified self-healing electrostatic (HA-SEL) actuators described in the paper titled "Hydraulically amplified self-healing electrostatic actuators with muscle-like performance" by E. Acome, S. K. Mitchell, T. G. Morrissey, M. B. Emmett, C. Benjamin, M. King, M. Radakovitz, and C. Keplinger (Science 5 Jan. 2018: Vol. 359, Issue 6371, pp. 61-65). Embodiments of the artificial muscle 101 including two pairs of tab portions 132, 154 on each of the first electrode 106 and the second electrode 108, respectively, reduces the overall mass and thickness of the artificial muscle 101, reduces the amount of voltage required during actuation, and decreases the total volume of the artificial muscle 101 without reducing the amount of resulting force after actuation as compared to known HASEL actuators including donut-shaped electrodes having a uniform, radially-extending width. More particularly, the tab portions 132, 154 of the artificial muscle 101 provide zipping fronts that result in increased actuation power by providing localized and uniform hydraulic actuation of the artificial muscle 101 compared to HASEL actuators including donut-shaped electrodes. Specifically, one pair of tab portions 132, 154 provides twice the amount of actuator power per unit volume as compared to donut-shaped HASEL actuators, while two pairs of tab portions 132, 154 provide four times the amount of actuator power per unit volume. The bridge portions 174, 176 interconnecting the tab portions 132, 154 also limit buckling of the tab portions 132, 154 by maintaining the distance between adjacent tab portions 132, 154 during actuation. Because the bridge portions 174, 176 are integrally formed with the tab portions 132, 154, the bridge portions 174, 176 also prevent leakage between the tab portions 132, 154 by eliminating attachment locations that provide an increased risk of rupturing.

Moreover, the size of the first electrode 106 and the second electrode 108 is proportional to the amount of displacement of the dielectric fluid 198. Therefore, when greater displacement within the expandable fluid region 196 is desired, the size of the electrode pair 104 is increased relative to the size of the expandable fluid region 196. It should be appreciated that the size of the expandable fluid region 196 is defined by the central openings 146, 168 in the first electrode 106 and the second electrode 108. Thus, the degree of displacement within the expandable fluid region 196 may alternatively, or in addition, be controlled by increasing or reducing the size of the central openings 146, 168.

In some embodiments, the first electrode 106 may not include a central opening. Thus, only the second electrode 108 includes the central opening 168 formed therein. In such embodiments, when the artificial muscle 101 is in the non-actuated state, the first electrode 106 is planar and the second electrode 108 is convex relative to the first electrode 106. In such embodiments, the SMA wire 50 may be coupled to the second plate 20B and extend therefrom to be coupled to a surface of the first electrode 106. It should be appreciated that by providing the central opening 168 only in the second electrode 108 as opposed to both the first electrode 106 and the second electrode 108, the total deformation may be formed on one side of the artificial muscle.

Figure 7:
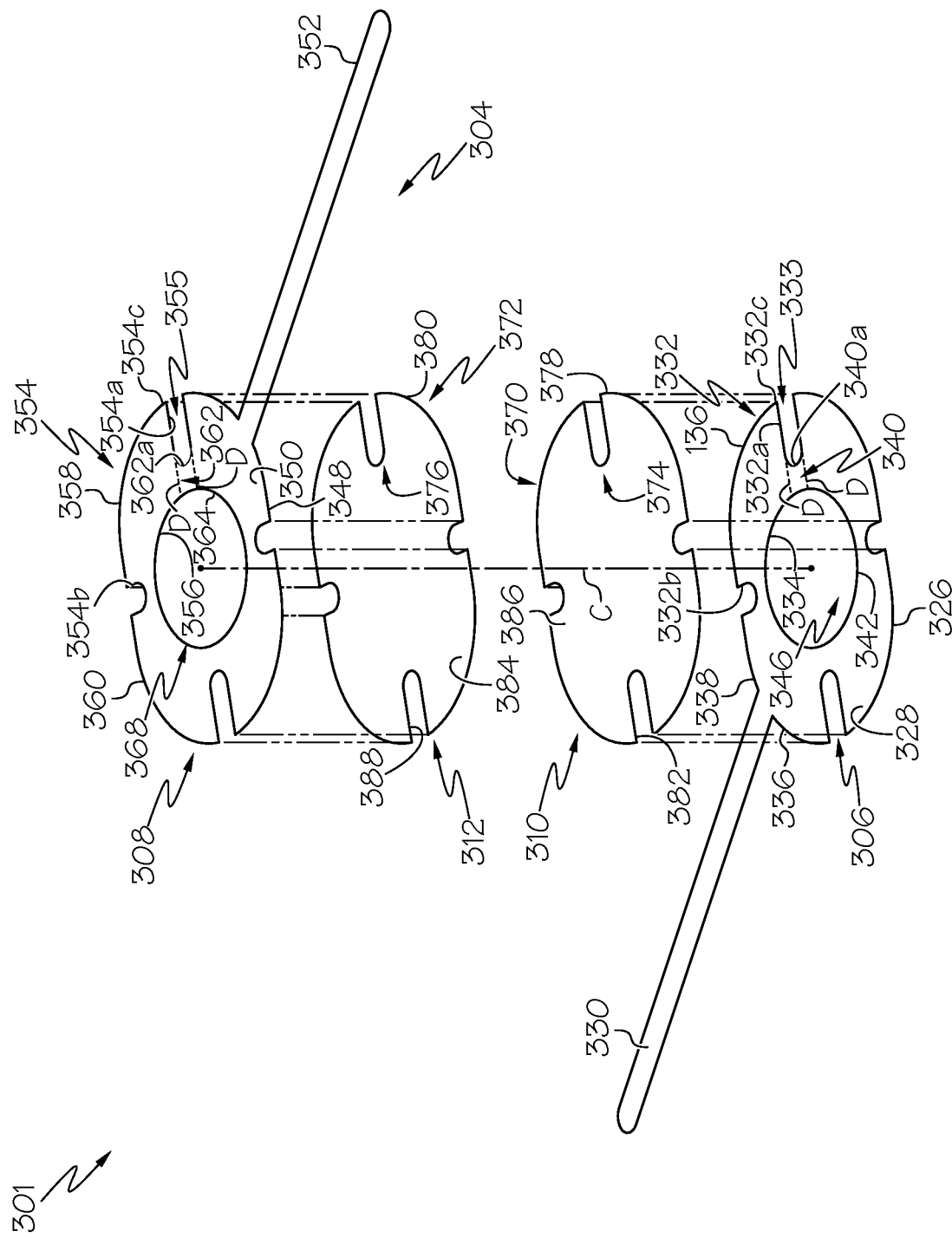
FIG. 7 schematically depicts an exploded view of another illustrative artificial muscle, according to one or more embodiments shown and described herein.
Figure 8:
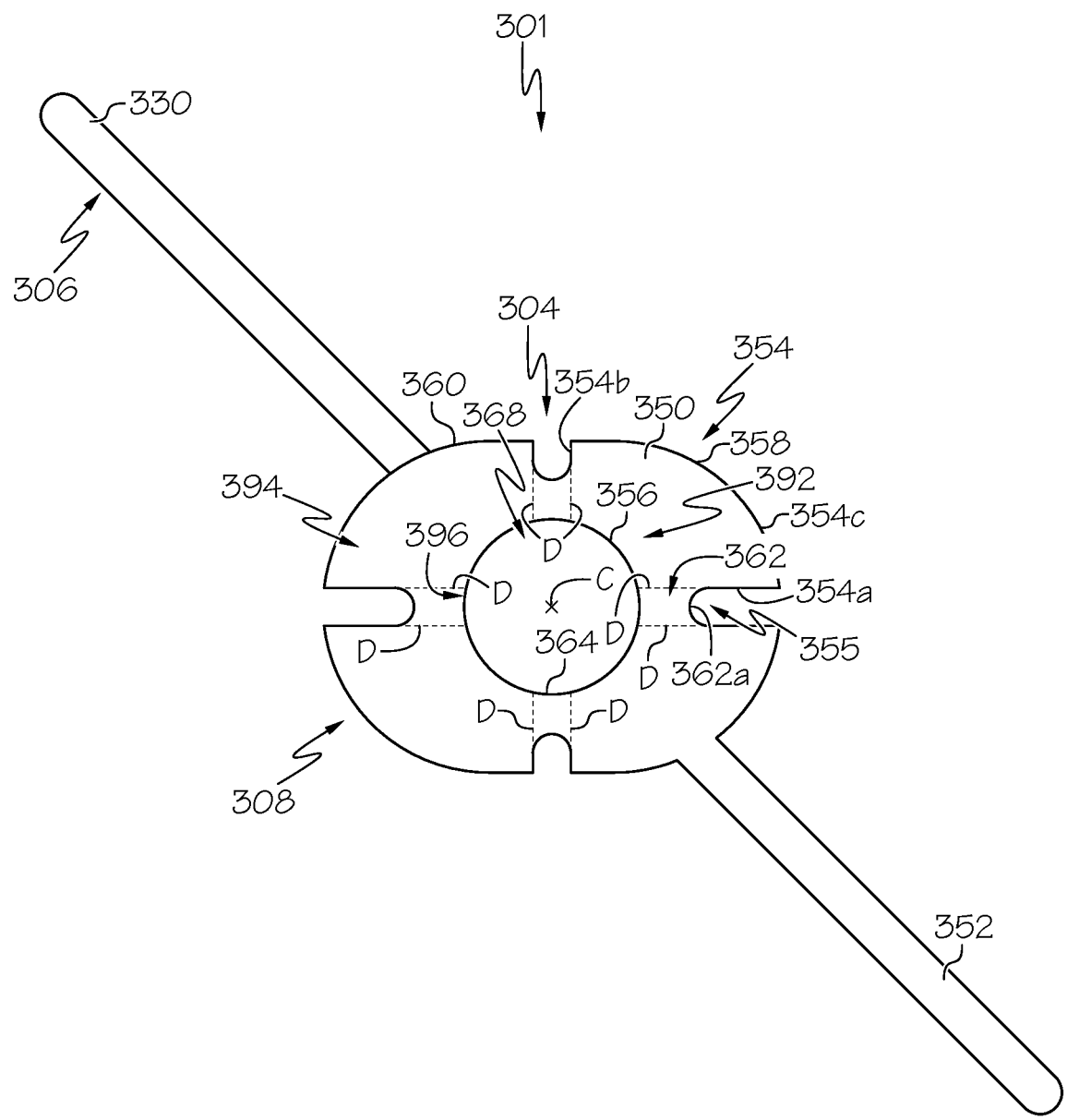
FIG. 8 schematically depicts a top view of the artificial muscle of FIG. 7, according to one or more embodiments shown and described herein.

As shown in FIGS. 7 and 8, another embodiment of an artificial muscle 301 is illustrated. It should be appreciated that the artificial muscle 301 includes similar structure as the artificial muscle 101 (FIGS. 3-6) and therefore operates similarly to the artificial muscle 101. Accordingly, the artificial muscle 301 described herein may be incorporated in the hybrid actuation device 10 (FIG. 1A-1B). Notably, the artificial muscle 301 includes fan portions 332 in place of the tab portions 132 discussed in relation to the artificial muscle 100. However, it should be understood that both the fan portions 332 of the artificial muscle 301 and the tab portions 132 are each generally a radially extending portion of an electrode of an artificial muscle, are positioned adjacent bridge portions, and provide a zipping functionality, as described above with respect to the artificial muscle 101, and below with respect to the artificial muscle 301. Indeed, these radially extending portions (e.g., tab portions and fan portions) each provide increased actuator power per unit volume, while minimizing buckling and rupture during operation.

Referring still to FIGS. 7 and 8, the artificial muscle 301 includes a housing (not shown) that is similar to the housing 110, an electrode pair 304, including a first electrode 306 and a second electrode 308, fixed to opposite surfaces of the housing, a first electrical insulator layer 310 fixed to the first electrode 306, and a second electrical insulator layer 312 fixed to the second electrode 308. In some embodiments, the housing is a one-piece monolithic layer including a surfaces that are heat-sealable. In other embodiments, the housing may be a pair of individually fabricated film layers.

The first electrode 306 and the second electrode 308 are each positioned within the housing. In some embodiments, the first electrode 306 and the second electrode 308 are each aluminum-coated polyester such as, for example, Mylar®. In addition, one of the first electrode 306 and the second electrode 308 is a negatively charged electrode and the other of the first electrode 306 and the second electrode 308 is a positively charged electrode. For purposes discussed herein, either electrode 306, 308 may be positively charged so long as the other electrode 306, 308 of the artificial muscle 301 is negatively charged.

The first electrode 306 has a film-facing surface 326 and an opposite inner surface 328. The first electrode 306 is positioned against the housing and include a first terminal 330 extending from the first electrode 306 past an edge of the housing such that the first terminal 330 can be connected to a power supply to actuate the first electrode 306. Specifically, the terminal is coupled, either directly or in series, to a power supply and a controller of the actuation system 400 (FIG. 10). Similarly, the second electrode 308 has a film-facing surface 348 and an opposite inner surface 350. The second electrode 308 may be positioned against the housing and include a second terminal 352 extending from the second electrode 308 past an edge of the housing such that the second terminal 352 can be connected to a power supply and a controller of the actuation system 400 (FIG. 10) to actuate the second electrode 308.

With respect now to the first electrode 306, the first electrode 306 includes two or more fan portions 332 extending radially from a center axis C of the artificial muscle 301. In some embodiments, the first electrode 306 includes only two fan portions 332 positioned on opposite sides or ends of the first electrode 306. In some embodiments, the first electrode 306 includes more than two fan portions 332, such as three, four, or five fan portions 332. In embodiments in which the first electrode 306 includes an even number of fan portions 332, the fan portions 332 may be arranged in two or more pairs of fan portions 332. As shown in FIG. 7, the first electrode 306 includes four fan portions 332. In this embodiment, the four fan portions 332 are arranged in two pairs of fan portions 332, where the two individual fan portions 332 of each pair are diametrically opposed to one another.

Each fan portion 332 has a first side edge 332a and an opposite second side edge 332b. As shown, the first terminal 330 extends from a second end 336 of one of the fan portions 332 and is integrally formed therewith. A channel 333 is at least partially defined by opposing side edges 332a, 332b of adjacent fan portions 332 and, thus, extends radially toward the center axis C. The channel 333 terminates at an end 340a of a bridge portion 340 interconnecting adjacent fan portions 332.

As shown in FIG. 7, dividing lines D are included to depict the boundary between the fan portions 332 and the bridge portions 340. The dividing lines D extend from the side edges 332a, 332b of the fan portions 332 to a first end 334 of the fan portions 332 collinear with the side edges 332a, 332b. It should be understood that dividing lines D are shown in FIG. 7 for clarity and that the fan portions 332 are integral with the bridge portions 340. The first end 334 of the fan portion 332, which extends between adjacent bridge portions 340, defines an inner length of the fan portion 332. Due to the geometry of the fan portion 332 tapering toward the center axis C between the first side edge 332a and the second side edge 332b, the second end 336 of the fan portion 332 defines an outer length of the fan portion 332 that is greater than the inner length of the fan portion 332.

Moreover, each fan portion 332 has a pair of corners 332c defined by an intersection of the second end 336 and each of the first side edge 332a and the second side edge 332b of the fan portion 332. In embodiments, the corners 332c are formed at an angle equal to or less than 90 degrees. In other embodiments, the corners 332c are formed at an acute angle.

As shown in FIG. 7, each fan portion 332 has a first side length defined by a distance between the first end 334 of the fan portion 332 and the second end 336 of the fan portion 332 along the first side edge 332a and the dividing line D that is collinear with the first side edge 332a. Each fan portion 332 also has a second side length defined by a distance between the first end 334 of the fan portion 332 and the second end 336 of the fan portion 332 along the second side edge 332b and the dividing line D that is collinear with the second side edge 332b. In embodiments, the first side length is greater than the second side length of the fan portion 332 such that the first electrode 306 has an ellipsoid geometry.

The second end 336, the first side edge 332a and the second side edge 332b of each fan portion 332, and the bridge portions 340 interconnecting the fan portions 332 define an outer perimeter 338 of the first electrode 306. In embodiments, a central opening 346 is formed within the first electrode 306 between the fan portions 332 and the bridge portions 340, and is coaxial with the center axis C. Each fan portion 332 has a fan length extending from a perimeter 342 of the central opening 346 to the second end 336 of the fan portion 332. Each bridge portion 340 has a bridge length extending from a perimeter 342 of the central opening 346 to the end 340a of the bridge portion 340, i.e., the channel 333. As shown, the bridge length of each of the bridge portions 340 is substantially equal to one another. Each channel 333 has a channel length defined by a distance between the end 340a of the bridge portion 340 and the second end of the fan portion 332. Due to the bridge length of each of the bridge portions 340 being substantially equal to one another and the first side length of the fan portions 332 being greater than the second side length of the fan portions 332, a first pair of opposite channels 333 has a channel length greater than a channel length of a second pair of opposite channels 333. As shown, a width of the channel 333 extending between opposing side edges 332a, 332b of adjacent fan portions 332 remains substantially constant due to opposing side edges 332a, 332b being substantially parallel to one another.

In embodiments, the central opening 346 has a radius of 2 centimeters (cm) to 5 cm. In embodiments, the central opening 346 has a radius of 3 cm to 4 cm. In embodiments, a total fan area of each of the fan portions 332 is equal to or greater than twice an area of the central opening 346. It should be appreciated that the ratio between the total fan area of the fan portions 332 and the area of the central opening 346 is directly related to a total amount of deflection of the housing when the artificial muscle 301 is actuated. In embodiments, the bridge length is 20% to 50% of the fan length. In embodiments, the bridge length is 30% to 40% of the fan length. In embodiments in which the first electrode 306 does not include the central opening 346, the fan length and the bridge length may be measured from a perimeter of an imaginary circle coaxial with the center axis C.

Similar to the first electrode 306, the second electrode 308 includes two or more fan portions 354 extending radially from the center axis C of the artificial muscle 301. The second electrode 308 includes substantially the same structure as the first electrode 306 and, thus, includes the same number of fan portions 354. Specifically, the second electrode 308 is illustrated as including four fan portions 354. However, it should be appreciated that the second electrode 308 may include any suitable number of fan portions 354.

Each fan portion 354 of the second electrode 308 has a first side edge 354a and an opposite second side edge 354b. As shown, the second terminal 352 extends from a second end 358 of one of the fan portions 354 and is integrally formed therewith. A channel 355 is at least partially defined by opposing side edges 354a, 354b of adjacent fan portions 354 and, thus, extends radially toward the center axis C. The channel 355 terminates at an end 362a of a bridge portion 362 interconnecting adjacent fan portions 354.

As shown in FIG. 7, additional dividing lines D are included to depict the boundary between the fan portions 354 and the bridge portions 362. The dividing lines D extend from the side edges 354a, 354b of the fan portions 354 to the first end 356 of the fan portions 354 collinear with the side edges 354a, 354b. It should be understood that dividing lines D are shown in FIG. 7 for clarity and that the fan portions 354 are integral with the bridge portions 362. The first end 356 of the fan portion 354, which extends between adjacent bridge portions 362, defines an inner length of the fan portion 354. Due to the geometry of the fan portion 354 tapering toward the center axis C between the first side edge 354a and the second side edge 354b, the second end 358 of the fan portion 354 defines an outer length of the fan portion 354 that is greater than the inner length of the fan portion 354.

Moreover, each fan portion 354 has a pair of corners 354c defined by an intersection of the second end 358 and each of the first side edge 354a and the second side edge 354b of the fan portion 354. In embodiments, the corners 354c are formed at an angle equal to or less than 90 degrees. In other embodiments, the corners 354c are formed at an acute angle. During actuation of the artificial muscle 301, the corners 332c of the first electrode 306 and the corners 354c of the second electrode 308 are configured to be attracted to one another at a lower voltage as compared to the rest of the first electrode 306 and the second electrode 308. Thus, actuation of the artificial muscle 301 initially at the corners 332c, 354c results in the outer perimeter 338 of the first electrode 306 and the outer perimeter 360 of the second electrode 308 being attracted to one another at a lower voltage and reducing the likelihood of air pockets or voids forming between the first electrode 306 and the second electrode 308 after actuation of the artificial muscle 301.

As shown in FIG. 7, in embodiments, the first side edge 354a of each fan portion 354 has a first side length defined by a distance between the first end 356 of the fan portion 354 and the second end 358 of the fan portion 354 along the first side edge 354a and the dividing line D that is collinear with the first side edge 354a. Each fan portion 354 also has a second side length defined by a distance between the first end 356 of the fan portion 354 and the second end 358 of the fan portion 354 along the second side edge 354b and the dividing line D that is collinear with the second side edge 354b. In embodiments, the first side length is greater than the second side length of the fan portion 354 such that the second electrode 308 has an ellipsoid geometry corresponding to the geometry of the first electrode 306.

The second end 358, the first side edge 354a and the second side edge 354b of each fan portion 354, and the bridge portions 362 interconnecting the fan portions 354 define an outer perimeter 360 of the second electrode 308. In embodiments, a central opening 368 is formed within the second electrode 308 between the fan portions 354 and the bridge portions 362, and is coaxial with the center axis C. Each fan portion 354 has a fan length extending from a perimeter 364 of the central opening 368 to the second end 358 of the fan portion 354. Each bridge portion 362 has a bridge length extending from the central opening 368 to the end 362a of the bridge portion 362, i.e., the channel 355. As shown, the bridge length of each of the bridge portions 362 is substantially equal to one another. Each channel 355 has a channel length defined by a distance between the end 362a of the bridge portion 362 and the second end of the fan portion 354. Due to the bridge length of each of the bridge portions 362 being substantially equal to one another and the first side length of the fan portions 354 being greater than the second side length of the fan portions 354, a first pair of opposite channels 355 has a channel length greater than a channel length of a second pair of opposite channels 355. As shown, a width of the channel 355 extending between opposing side edges 354a, 354b of adjacent fan portions 354 remains substantially constant due to opposing side edges 354a, 354b being substantially parallel to one another.

In embodiments, the central opening 368 has a radius of 2 cm to 5 cm. In embodiments, the central opening 368 has a radius of 3 cm to 4 cm. In embodiments, a total fan area of each of the fan portions 354 is equal to or greater than twice an area of the central opening 368. It should be appreciated that the ratio between the total fan area of the fan portions 354 and the area of the central opening 368 is directly related to a total amount of deflection of the housing when the artificial muscle 301 is actuated. In embodiments, the bridge length is 20% to 50% of the fan length. In embodiments, the bridge length is 30% to 40% of the fan length. In embodiments in which the second electrode 308 does not include the central opening 368, the fan length and the bridge length may be measured from a perimeter of an imaginary circle coaxial with the center axis C.

As described herein, the first electrode 306 and the second electrode 308 each have a central opening 346, 368 coaxial with the center axis C. However, it should be understood that the first electrode 306 does not need to include the central opening 346 when the central opening 368 is provided within the second electrode 308. Alternatively, the second electrode 308 does not need to include the central opening 368 when the central opening 346 is provided within the first electrode 306.

Referring again to FIG. 7, the first electrical insulator layer 310 and the second electrical insulator layer 312 have a substantially ellipsoid geometry generally corresponding to the geometry of the first electrode 306 and the second electrode 308, respectively. Thus, the first electrical insulator layer 310 and the second electrical insulator layer 312 each have fan portions 370, 372 and bridge portions 374, 376 corresponding to like portions on the first electrode 306 and the second electrode 308. Further, the first electrical insulator layer 310 and the second electrical insulator layer 312 each have an outer perimeter 378, 380 corresponding to the outer perimeter 338 of the first electrode 306 and the outer perimeter 360 of the second electrode 308, respectively, when positioned thereon.

It should be appreciated that, in some embodiments, the first electrical insulator layer 310 and the second electrical insulator layer 312 generally include the same structure and composition. As such, in some embodiments, the first electrical insulator layer 310 and the second electrical insulator layer 312 each include an adhesive surface 382, 384 and an opposite non-sealable surface 386, 388, respectively. Thus, in some embodiments, the first electrical insulator layer 310 and the second electrical insulator layer 312 are each a polymer tape adhered to the inner surface 328 of the first electrode 306 and the inner surface 350 of the second electrode 308, respectively.

Referring now to FIG. 8, the artificial muscle 301 is shown in its assembled form with the first terminal 330 of the first electrode 306 and the second terminal 352 of the second electrode 308 extending past an outer perimeter of the housing The second electrode 308 is stacked on top of the first electrode 306 and, therefore, the housing is not shown. In its assembled form, the first electrode 306, the second electrode 308, the first electrical insulator layer 310 (FIG. 7), and the second electrical insulator layer 312 (FIG. 7) are sandwiched within the housing. The housing is partially sealed at an area surrounding the outer perimeter 338 (FIG. 7) of the first electrode 306 and the outer perimeter 360 of the second electrode 308. In some embodiments, the housing may heat seal at a sealed portion 390 surrounding the first electrode 306 and the second electrode 308. The housing may be sealed in any suitable manner, such as using an adhesive, heat sealing, vacuum sealing, or the like.

The first electrode 306, the second electrode 308, the first electrical insulator layer 310 (FIG. 7), and the second electrical insulator layer 312 (FIG. 7) provide a barrier that prevents the housing from heat sealing at an unsealed portion 392. The unsealed portion 392 of the housing includes an electrode region 394, in which the electrode pair 304 is provided, and an expandable fluid region 396, which is surrounded by the electrode region 394. The central openings 346 (FIG. 7), 368 of the first electrode 306 and the second electrode 308 define the expandable fluid region 396 and are arranged to be axially stacked on one another. Although not shown, the housing may be cut to conform to the geometry of the electrode pair 304 and reduce the size of the artificial muscle 301, namely, the size of the sealed portion 390. A dielectric fluid is provided within the unsealed portion 392 and flows freely between the first electrode 306 and the second electrode 308

Referring still to FIGS. 7 and 8, actuation of the artificial muscle 301 will be discussed. In the non-actuated state, the first electrode 306 and the second electrode 308 are partially spaced apart from one another proximate the central openings 346, 368 thereof and the first end 334, 356 of the fan portions 332, 354. The second end 336, 358 of the fan portions 332, 354 remain in position relative to one another due to the housing being sealed at the outer perimeter 338 of the first electrode 306 and the outer perimeter 360 of the second electrode 308. In the actuated state, the first electrode 306 and the second electrode 308 are brought into contact with and oriented parallel to one another to force the dielectric fluid (not shown) into the expandable fluid region 396. This causes the dielectric fluid to flow through the central openings 346, 368 of the first electrode 306 and the second electrode 308 and inflate the expandable fluid region 396.

In the non-actuated state, a distance between the first end 334 of the fan portion 332 of the first electrode 306 and the first end 356 of the fan portion 354 of the second electrode 308 is greater than a distance between the second end 336 of the fan portion 332 of the first electrode 306 and the second end 358 of the fan portion 354 of the second electrode 308. This results in the electrode pair 304 zippering toward the expandable fluid region 396 when actuated. When actuated, the first electrode 306 and the second electrode 308 zipper toward one another from the second ends 336, 358 of the fan portions 332, 354 thereof, thereby pushing the dielectric fluid into the expandable fluid region 396. When in the actuated state, the first electrode 306 and the second electrode 308 are parallel to one another. In the actuated state, the dielectric fluid flows into the expandable fluid region 396 to inflate the expandable fluid region 396. As such, the housing expands in opposite directions.

Figure 9:
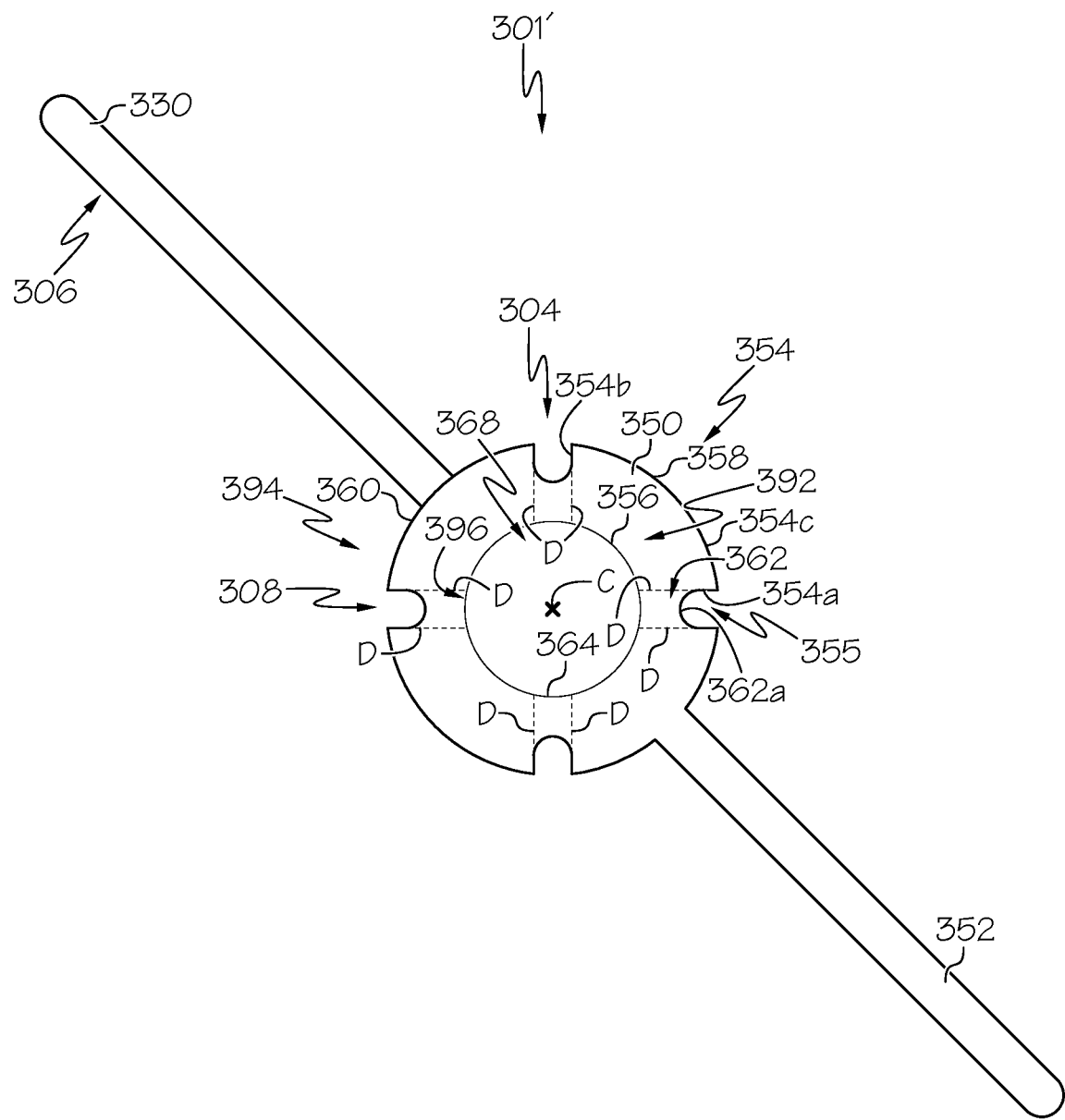
FIG. 9 schematically depicts a top view of another artificial muscle, according to one or more embodiments shown and described herein.

Referring now to FIG. 9, an alternative embodiment of an artificial muscle 301' is illustrated. It should be appreciated that the artificial muscle 301' is similar to the artificial muscle 301 described herein. As such, like structure is indicated with like reference numerals. The first electrode 306 and the second electrode 308 of the artificial muscle 301' have a circular geometry as opposed to the ellipsoid geometry of the first electrode 306 and the second electrode 308 of the artificial muscle 301 described herein. As shown in FIG. 9, with respect to the second electrode 308, a first side edge length of the first side edge 354*a* is equal to a second side edge length of the second side edge 354*b*. Accordingly, the channels 355 formed between opposing side edges 354*a*, 354*b* of the fan portions 354 each have an equal length. Although the first electrode 306 is hidden from view in FIG. 9 by the second electrode 308, it should be appreciated that the first electrode 306 also has a circular geometry corresponding to the geometry of the second electrode 308.

Referring now to FIG. 10, an actuation system 400 may be provided for operating the hybrid actuation devices 10, 10', in particular, the artificial muscles 100, 101, 301, 301', and the SMA wire 50 of the hybrid actuation device 10. The actuation system 400 may comprise a controller 410, an operating device 420, a power supply 430, a display device 440, network interface hardware 450, and a communication path 405 communicatively coupled these components, some or all of which may be disposed in the onboard control unit 402.

The controller 410 may comprise a processor 412 and a non-transitory electronic memory 414 to which various components are communicatively coupled. In some embodiments, the processor 412 and the non-transitory electronic memory 414 and/or the other components are included within a single device. In other embodiments, the processor 412 and the non-transitory electronic memory 414 and/or the other components may be distributed among multiple devices that are communicatively coupled. The controller 410 may include non-transitory electronic memory 414 that stores a set of machine-readable instructions. The processor 412 may execute the machine-readable instructions stored in the non-transitory electronic memory 414. The non-transitory electronic memory 414 may comprise RAM, ROM, flash memories, hard drives, or any device capable of storing machine-readable instructions such that the machine-readable instructions can be accessed by the processor 412. Accordingly, the actuation system 400 described herein may be implemented in any computer programming language, as pre-programmed hardware elements, or as a combination of hardware and software components. The non-transitory electronic memory 414 may be implemented as one memory module or a plurality of memory modules.

In some embodiments, the non-transitory electronic memory 414 includes instructions for executing the functions of the actuation system 400. The instructions may include instructions for operating the hybrid actuation device 10, for example, instructions for actuating the artificial muscles 100 and actuating the SMA wires 50.

The processor 412 may be any device capable of executing machine-readable instructions. For example, the processor 412 may be an integrated circuit, a microchip, a computer, or any other computing device. The non-transitory electronic memory 414 and the processor 412 are coupled to the communication path 405 that provides signal interconnectivity between various components and/or modules of the actuation system 400. Accordingly, the communication path 405 may communicatively couple any number of processors with one another, and allow the modules coupled to the communication path 405 to operate in a distributed computing environment. Specifically, each of the modules may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

As schematically depicted in FIG. 10, the communication path 405 communicatively couples the processor 412 and the non-transitory electronic memory 414 of the controller 410 with a plurality of other components of the actuation system 400. For example, the actuation system 400 depicted in FIG. 10 includes the processor 412 and the non-transitory electronic memory 414 communicatively coupled with the operating device 420 and the power supply 430.

The operating device 420 allows for a user to control operation of the artificial muscles 100 and the SMA wire 50 of the hybrid actuation device 10. In some embodiments, the operating device 420 may be a switch, toggle, button, or any combination of controls to provide user operation. The operating device 420 is coupled to the communication path 405 such that the communication path 405 communicatively couples the operating device 420 to other modules of the actuation system 400. The operating device 420 may provide a user interface for receiving user instructions as to a specific operating configuration of the hybrid actuation device 10, such as an amount desired actuation.

The power supply 430 (e.g., battery) provides power to the artificial muscle 100, such as by power supply 430A, and the SMA wire 50, such as by the power supply 430B. In some embodiments, the power supply 430, which includes the power supply 430A and the power supply 430B, is a rechargeable direct current power supply. It is to be understood that the power supply 430 may be a single power supply or battery for providing power to the artificial muscle 100 and the SMA wire 50 of the hybrid actuation device 10. A power adapter (not shown) may be provided and electrically coupled via a wiring harness or the like for providing power to the artificial muscle 100 and the SMA wire 50 of the hybrid actuation device 10 via the power supply 430. Indeed, the power supply 430 is a device that can receive power at one level (e.g., one voltage, power level, or current) and output power at a second level (e.g., a second voltage, power level, or current).

In some embodiments, the actuation system 400 also includes a display device 440. The display device 440 is coupled to the communication path 405 such that the communication path 405 communicatively couples the display device 440 to other modules of the actuation system 400. The display device 440 may be located on the hybrid actuation device 10, for example, as part of the onboard control unit 402, and may output a notification in response to an actuation state of hybrid actuation device 10 or indication of a change in the actuation state of the hybrid actuation device 10. The display device 440 may be a touchscreen that, in addition to providing optical information, detects the presence and location of a tactile input upon a surface of or adjacent to the display device 440. Accordingly, the display device 440 may include the operating device 420 and receive mechanical input directly upon the optical output provided by the display device 440. For example, a user may be able to specify a desired actuation pressure value.

In some embodiments, the actuation system 400 includes network interface hardware 450 for communicatively coupling the actuation system 400 to a portable device 460 via a network 470. The portable device 460 may include, without limitation, a smartphone, a tablet, a personal media player, or any other electric device that includes wireless communication functionality. The portable device 460 may correspond to an infotainment device, or any other type of device capable of communicating with the network interface hardware 450, utilizing Wi-Fi, Bluetooth, and/or any other suitable communication protocol. It is to be appreciated that, when provided, the portable device 460 may serve to provide user commands to the controller 410, instead of the operating device 420. As such, a user may be able to control or set a program for controlling the hybrid actuation device 10 utilizing the controls of the operating device 420. Thus, the hybrid actuation device 10 may be controlled remotely via the portable device 460 wirelessly communicating with the controller 410 via the network 470. For example, the user may be able to specify a desired actuation force value.

It should now be understood that embodiments described herein to hybrid actuation devices that include an SMA wire and an artificial muscle. The artificial muscle is positioned between and coupled to a plate pair and the SMA wire is coupled to the plate pair. Application of a stimulant such as current flow in the SMA wire contracts the SMA wire and closes the plate pair together, placing the hybrid actuation device in an actuated state. The first and second electrode electrostatically attract upon application of a voltage to hold the hybrid actuation device in the actuated state allowing actuation (e.g., contraction) of the SMA wire to cease while retaining the hybrid actuation device in the actuated state. The hybrid actuation device combines the actuation force achievable with an SMA wire and the displacement achievable with an artificial muscle to provide an improved actuation device.

While particular embodiments have been illustrated and described herein, it should be understood that various other changes and modifications may be made without departing from the scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A hybrid actuation device comprising:
   an artificial muscle comprising:
      a housing including a first film layer and a second film layer, the housing having an electrode region and an expandable fluid region;
      a first electrode and a second electrode each disposed in the electrode region of the housing; and
      a dielectric fluid disposed within the housing;
   a first plate coupled to a second plate and positioned within the housing, the first plate positioned between the first film layer and the first electrode, and the second plate positioned between the second film layer and the second electrode; and
   a shape memory alloy wire extending from the first plate to the second plate and extending through the dielectric fluid.

2. The hybrid actuation device of claim 1, the expandable fluid region of the housing is positioned apart from a perimeter of the first plate and the second plate.

3. The hybrid actuation device of claim 1, wherein the first plate and the second plate each comprises a first end and an opposite second end, the second end of the first plate is pivotally coupled to the second end of the second plate by a hinge.

4. The hybrid actuation device of claim 3, wherein the first plate and the second plate each comprises a central portion and an overhanging portion, the central portion being coupled to the first electrode, the overhanging portion extending away from the central portion to be spaced apart from the first electrode, and the shape memory alloy wire being coupled to the first plate at the overhanging portion.

5. The hybrid actuation device of claim 1, wherein the first plate is partially heat sealed to the first film layer at a first sealed region adjacent a first unsealed region coaxial with the expandable fluid region, a first protective film is positioned between the first film layer and the first plate at the first unsealed region to prevent the first film layer from heat sealing to the first plate at the first unsealed region, the shape memory alloy wire being provided within the first unsealed region.

6. The hybrid actuation device of claim 1, further comprising a plurality of plate pairs each comprising a first plate coupled to a second plate.

7. The hybrid actuation device of claim 6, wherein the first plate and the second plate of each of the plurality of plate pairs have an annular sector shape such that the plurality of plate pairs form an annular plate system, the housing extending over each of the plurality of plate pairs.

8. The hybrid actuation device of claim 7, wherein each of the plurality of plate pairs comprises a shape memory alloy wire coupling the first plate of each of the plurality of plate pairs to a respective second plate of the plurality of plate pairs.

9. The hybrid actuation device of claim 8, wherein the first plate of each of the plurality of plate pairs cooperate to define a central portion and an overhanging portion, the central portion being coupled to the first electrode, the overhanging portion extending away from the central portion to be spaced apart from the first electrode, and the shape memory alloy wires being coupled to the respective first plate at the overhanging portion.

10. The hybrid actuation device of claim 9, further comprising a first protective film coupled to the overhanging portion of the first plate of each of the plurality of plate pairs, wherein:
   the first electrode and the second electrode each comprises two or more radially extending portions and two or more bridge portions;
   each of the two or more bridge portions interconnects adjacent radially extending portions;
   the first electrode comprises a central opening positioned between the two or more radially extending portions and encircling the expandable fluid region; and
   the first protective film extends over the central opening of the first electrode.

11. The hybrid actuation device of claim 10, further comprising a second protective film coupled to the overhanging portion of the second plate of each of the plurality of plate pairs, wherein:
   the second electrode comprises a central opening positioned between the two or more radially extending portions and encircling the expandable fluid region; and
   the second protective film extends over the central opening of the second electrode.

12. A hybrid actuation device comprising:
   an artificial muscle comprising:
      a housing having an electrode region and an expandable fluid region;
      a first electrode and a second electrode each disposed in the electrode region of the housing, a central opening formed in each of the first electrode and the second electrode and encircling the expandable fluid region; and
      a dielectric fluid disposed within the housing;

a plate system comprising a plurality of plate pairs, each of the plurality of plate pairs comprising a first plate coupled to a second plate, the first plate and the second plate positioned within the housing; and a shape memory alloy wire coupled to at least one first plate of the plurality of plate pairs, the shape memory alloy wire positioned within the central opening of the first electrode and the second electrode.

13. The hybrid actuation device of claim 12, wherein the shape memory alloy wire extends from the first plate through the expandable fluid region to be coupled to the second plate.

14. The hybrid actuation device of claim 13, wherein the first plate and the second plate each comprises a first end and an opposite second end, the second end of the first plate is pivotally coupled to the second end of the second plate by a hinge.

15. The hybrid actuation device of claim 14, wherein:

each first plate of the plurality of plate pairs cooperate to define a central portion and an overhanging portion, the central portion being coupled to the first electrode, the overhanging portion extending away from the central portion to be spaced apart from the first electrode and positioned in the expandable fluid region, and the shape memory alloy wire is coupled to and extends from the first plate at the overhanging portion.

16. The hybrid actuation device of claim 12, wherein the first electrode comprises two or more radially extending portions and two or more bridge portions, each of the two or more bridge portions interconnects adjacent radially extending portions, and the central opening is positioned between the two or more radially extending portions.

17. A method of actuating a hybrid actuation device, the method comprising:

actuating a shape memory alloy wire that is coupled to a first plate and a second plate, thereby drawing the first plate and the second plate together and placing the hybrid actuation device in an actuated state, wherein an artificial muscle is at least partially positioned between the first plate and the second plate, the artificial muscle comprising:

a housing including a first film layer and a second film layer, the housing having an electrode region and an expandable fluid region;

a first electrode and a second electrode each disposed in the electrode region of the housing; and a dielectric fluid disposed within the housing, wherein the shape memory alloy wire extends from the first plate to the second plate and extends through the dielectric fluid, the first plate is positioned within the housing between the first film layer and the first electrode, and the second plate is positioned within the housing between the second film layer and the second electrode; and applying a voltage to the first electrode and the second electrode, thereby electrostatically attracting the first electrode and the second electrode together to hold the hybrid actuation device in the actuated state.

18. The method of claim 17, wherein the expandable fluid region is positioned apart from the first plate and the second plate such that drawing the first plate and the second plate together directs the dielectric fluid into the expandable fluid region, thereby expanding the expandable fluid region.

19. The method of claim 18, wherein actuating the shape memory alloy wire comprises one or more of:

directing a current through the shape memory alloy wire;

heating the shape memory alloy wire; and applying a magnetic field to the shape memory alloy wire.

20. The method of claim 17, wherein actuating the shape memory alloy wire contracts the shape memory alloy wire, thereby drawing the first plate and the second plate together.

* * * * *